US012062153B2

(12) United States Patent
Lu et al.

(10) Patent No.: US 12,062,153 B2
(45) Date of Patent: Aug. 13, 2024

(54) APPARATUS, METHOD, AND NON-TRANSITORY COMPUTER-READABLE STORAGE MEDIUM FOR IMPROVING IMAGE QUALITY OF A MEDICAL IMAGE VOLUME

(71) Applicant: CANON MEDICAL SYSTEMS CORPORATION, Otawara (JP)

(72) Inventors: Yujie Lu, Vernon Hills, IL (US); Qiulin Tang, Vernon Hills, IL (US); Zhou Yu, Vernon Hills, IL (US); Jian Zhou, Vernon Hills, IL (US)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 525 days.

(21) Appl. No.: 17/369,596

(22) Filed: Jul. 7, 2021

(65) Prior Publication Data
US 2023/0011759 A1    Jan. 12, 2023

(51) Int. Cl.
*G06T 5/20*    (2006.01)
*G06N 3/08*    (2023.01)
(Continued)

(52) U.S. Cl.
CPC ............... *G06T 5/20* (2013.01); *G06N 3/08* (2013.01); *G06T 5/50* (2013.01); *G16H 30/40* (2018.01);
(Continued)

(58) Field of Classification Search
None
See application file for complete search history.

(56) References Cited

U.S. PATENT DOCUMENTS

2013/0051519 A1    2/2013  Yang et al.
2019/0180481 A1*   6/2019  Fu ..................... G06T 11/006
(Continued)

FOREIGN PATENT DOCUMENTS

CN    111210444 A        5/2020
CN    111292386 A   *    6/2020   ........... G06N 3/0454
(Continued)

OTHER PUBLICATIONS

Liu, Tao et al. "Pseudo-3D Network for Multi-sequence Cardiac MR Segmentation," STACOM 2019, LNCS 12009, pp. 237-245, 2020. https://github.com/liut969/Multi-sequence-Cardiac-MR-Segmentation.
(Continued)

*Primary Examiner* — Jiangeng Sun
(74) *Attorney, Agent, or Firm* — Oblon, McClelland, Maier & Neustadt, L.L.P.

(57) ABSTRACT

An apparatus, method, and computer-readable medium for improving image quality of a medical volume. In an embodiment, the apparatus includes processing circuitry configured to receive a reconstructed input image volume from X-ray projection data corresponding to a three-dimensional region of an object to be examined, apply a pseudo-three-dimensional neural network (P3DNN) to the reconstructed input image volume, the application of the pseudo-three-dimensional neural network including generating, for the reconstructed input image volume, a plurality of three-dimensional image datasets representing a different anatomical plane of the reconstructed input image volume, applying at least one convolutional filter to each of a sagittal plane dataset, a transverse plane dataset, and a coronal plane dataset, and concatenating results of the applied at least one convolutional filter to generate an intermediate output image volume, and generate, based on the application of the
(Continued)

P3DNN, an output image volume corresponding to the three-dimensional region of the object.

16 Claims, 14 Drawing Sheets

(51) Int. Cl.
    *G06T 5/50*     (2006.01)
    *G16H 30/40*     (2018.01)

(52) U.S. Cl.
    CPC . *G06T 2200/04* (2013.01); *G06T 2207/10116* (2013.01); *G06T 2207/20081* (2013.01); *G06T 2207/20084* (2013.01); *G06T 2207/30004* (2013.01)

(56) References Cited

U.S. PATENT DOCUMENTS

| | | | |
|---|---|---|---|
| 2020/0034948 A1* | 1/2020 | Park | G06N 20/20 |
| 2020/0234471 A1 | 7/2020 | Lu et al. | |
| 2020/0305806 A1 | 10/2020 | Tang et al. | |
| 2020/0349699 A1 | 11/2020 | Shah | |

FOREIGN PATENT DOCUMENTS

| | | | | |
|---|---|---|---|---|
| CN | 110969245 B | | 7/2020 | |
| CN | 112885453 A | * | 6/2021 | G06N 3/08 |
| EP | 3504680 B1 | * | 4/2023 | A61N 5/10 |
| WO | WO-2017011532 A1 | * | 1/2017 | |
| WO | WO-2019241266 A1 | * | 12/2019 | |
| WO | WO 2020/198854 A1 | | 10/2020 | |

OTHER PUBLICATIONS

Vu, Minh H. et al. "Evaluation of Multi-Slice Inputs to Convolutional Neural Networks for Medical Image Segmentation," Jun. 13, 2020. https://www.researchgate.net/publication/33806473.

Shan, Hongming et al. "3D Convolutional Encoder-Decoder Network for Low-Dose CT via Transfer Learning from a 2D Trained Network," IEEE Transactions of Medical Imaging. arXiv:1802.05656v2 [cs.CV] Apr. 29, 2018.

Qiu, Zhaofan et al. "Learning Spatio-Temporal Representation with Pseudo-3D Residual Networks" 2017.

Du, Wenchao et al. Stacked competitive networks for noise reduction in low-dose CT. PLoS One 12(12): e0190069. Dec. 21, 2017 https://doi.org/10.1371/journal.pone.0190069.

Wolterink, Jelmer M. et al. "Generative Adversarial Networks for Noise Reduction in Low-Dose CT," IEEE Transactions on Medical Imaging, vol. 36, No. 12, Dec. 2017.

Mentl, Katrin et al. "Noise Reduction in Low-Dose CT Using a 3D Multiscale Sparse Denoising Autoencoder," 2017 IEEE International Workshop on Machine Learning for Signal Processing, Sep. 25-28, 2017, Tokyo, Japan.

Q. Yang, et al, Low dose CT image denoising using a generative adversarial network with wasserstein distance and perceptual loss. 2018.

E. Kang, et al, Wavelet domain residual network (WavResNet) for low-dose x-ray CT reconstruction. 2017.

H.Chen, et al, Low-dose CT with a residual encoder-decoder convolutional neural network (RED-CNN), 2017.

D. Wu, et al, Iterative low-dose CT reconstruction with priors trained by artificial neural network. 2017.

Q. Yang, et al, CT image denoising with perceptive deep neural networks. 2017.

* cited by examiner

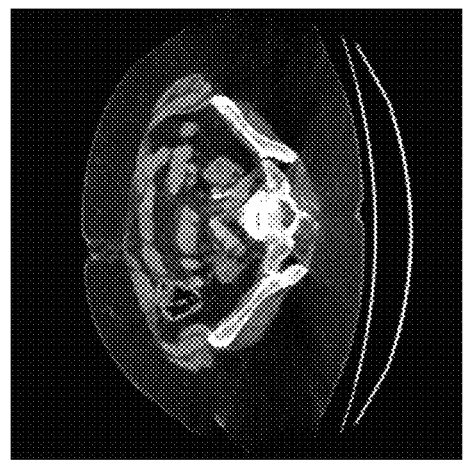
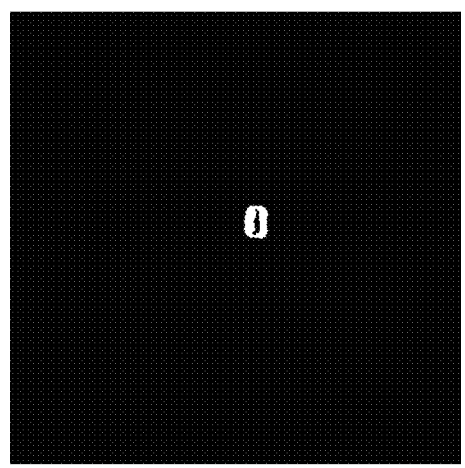
FIG. 6B

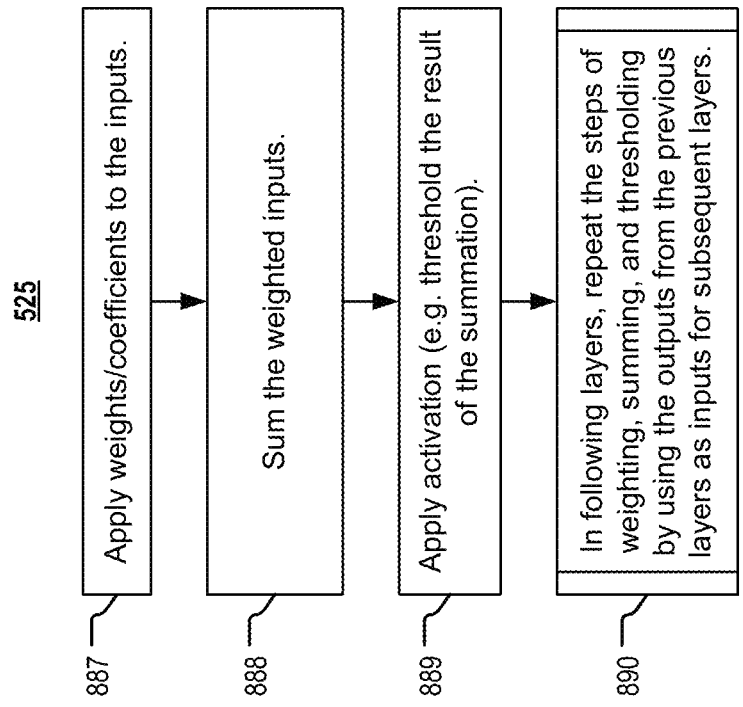

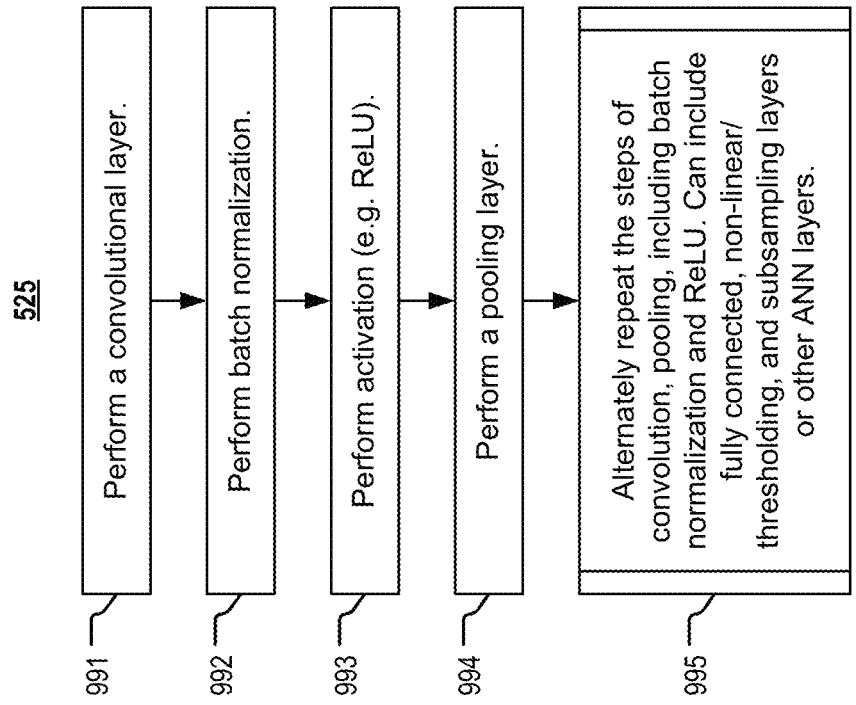

APPARATUS, METHOD, AND NON-TRANSITORY COMPUTER-READABLE STORAGE MEDIUM FOR IMPROVING IMAGE QUALITY OF A MEDICAL IMAGE VOLUME

BACKGROUND

Field of the Disclosure

The present disclosure relates to improving image quality in medical imaging. In particular, the present disclosure relates to noise reduction in a medical image volume. The present disclosure also relates to super-resolution.

Description of the Related Art

In computed tomography (CT) scanning, image quality can be described as a function of spatial resolution, contrast, image noise, artifacts, and the like. While image quality has, of course, always been a concern for the physics community, clinically acceptable image quality has become increasingly relevant as strategies to reduce radiation exposure to the patient become a larger focus. This goal, however, is challenged by the fact that higher radiation doses often result in reduced influence of image noise and improvements in perception of low-contrast structures. As such, a method for improving image quality and, in particular, reducing image noise, while minimizing radiation exposure to the patient, has been a recent focus of researchers.

To this end, deep learning-based machine learning methods, such as deep convolutional neural networks (DCNN), have been readily applied. Such DCNN-based approaches have been applied to CT projection pre-correction, image reconstruction, and image post-processing, which can include denoising and artifact reduction, and have achieved promising results. The DCNN-based method utilizes a multi-layer network to extract image features from offline training data with end-to-end iterative training. In this way, as it relates to noise reduction, DCNN-based denoising networks can achieve adequate image quality from low-dose images by learning improved noise texture from high-dose images.

Unfortunately, almost all deep learning-based machine learning denoising methods learn high-dose noise texture from CT images in only a transverse direction using a two-dimensional (2D) network. When such a transverse direction-2D denoising network is applied, the image quality along the longitudinal direction, including noise texture, is affected. Furthermore, due to reconstruction properties, such as a ramp filter applied along the transverse direction during analytical reconstruction, noise texture is different between anatomical directions (e.g., transverse direction, longitudinal direction). Thus, the adverse effect of only applying a transverse direction-2D denoising network is amplified. While a three-dimensional (3D) DCNN-based denoising network could be applied to solve the problem, the computational bulk of the 3D DCNN-based denoising network significantly reduces denoising speed. Therefore, users are left with no tools that account for, among other factors, noise texture differences across anatomical directions while also providing expedient denoising.

The foregoing "Background" description is for the purpose of generally presenting the context of the disclosure. Work of the inventors, to the extent it is described in this background section, as well as aspects of the description which may not otherwise qualify as prior art at the time of filing, are neither expressly or impliedly admitted as prior art against the present invention.

SUMMARY

The present disclosure relates to a method for improving image quality of a medical image volume. In a preferred embodiment, the medical image volume is a reconstruction of X-ray projection data from a computed tomography scanner.

In an embodiment, the present disclosure further relates to an apparatus for improving image quality of a medical image volume, the apparatus comprising processing circuitry configured to receive a reconstructed input image volume from X-ray projection data corresponding to a three-dimensional region of an object to be examined, apply a pseudo-three-dimensional neural network to the reconstructed input image volume, the application of the pseudo-three-dimensional neural network including generating, for the reconstructed input image volume, a plurality of three-dimensional image datasets representing a different anatomical plane of the reconstructed input image volume, the plurality of three-dimensional image datasets including a sagittal plane dataset, a transverse plane dataset, and a coronal plane dataset, applying at least one convolutional filter to each of the sagittal plane dataset, the transverse plane dataset, and the coronal plane dataset, and concatenating results of the applied at least one convolutional filter to generate an intermediate output image volume, and generate, based on the application of the pseudo-three-dimensional neural network, an output image volume corresponding to the three-dimensional region of the object and having improved image quality.

In an embodiment, the present disclosure further relates to a method for improving image quality of a medical image volume, the method comprising receiving, by processing circuitry, a reconstructed input image volume from X-ray projection data corresponding to a three-dimensional region of an object to be examined, applying, by the processing circuitry, a pseudo-three-dimensional neural network to the reconstructed input image volume, the application of the pseudo-three-dimensional neural network including generating, by the processing circuitry and for the reconstructed input image volume, a plurality of three-dimensional image datasets representing a different anatomical plane of the reconstructed input image volume, the plurality of three-dimensional image datasets including a sagittal plane dataset, a transverse plane dataset, and a coronal plane dataset, applying, by the processing circuitry, at least one convolutional filter to each of the sagittal plane dataset, the transverse plane dataset, and the coronal plane dataset, and concatenating, by the processing circuitry, results of the applied at least one convolutional filter to generate an intermediate output image volume; and generating, by the processing circuitry and based on the application of the pseudo-three-dimensional neural network, an output image volume corresponding to the three-dimensional region of the object and having improved image quality.

In an embodiment, the present disclosure further relates to a non-transitory computer-readable storage medium storing computer-readable instructions that, when executed by a computer, cause the computer to perform a method for improving image quality of a medical image volume, comprising receiving a reconstructed input image volume from X-ray projection data corresponding to a three-dimensional region of an object to be examined, applying a pseudo-threedimensional neural network to the reconstructed input image volume, the application of the pseudo-three-dimensional neural network including generating, for the reconstructed input image volume, a plurality of three-dimensional image datasets representing a different anatomical plane of the reconstructed input image volume, the plurality of three-dimensional image datasets including a sagittal plane dataset, a transverse plane dataset, and a coronal plane dataset, applying at least one convolutional filter to each of the sagittal plane dataset, the transverse plane dataset, and the coronal plane dataset, and concatenating results of the applied at least one convolutional filter to generate an intermediate output image volume, and generating, based on the application of the pseudo-three-dimensional neural network, an output image volume corresponding to the three-dimensional region of the object and having improved image quality.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein:

FIG. 6B is a graphical illustration of a sub process for determining weights of a parameter of a loss function, according to an exemplary embodiment of the present disclosure;

FIG. 8 is a generalized flow diagram of implementation of an artificial neural network;

FIG. 9 is a flow diagram of implementation of a convolutional neural network, according to an exemplary embodiment of the present disclosure;

DETAILED DESCRIPTION

Figure 1:
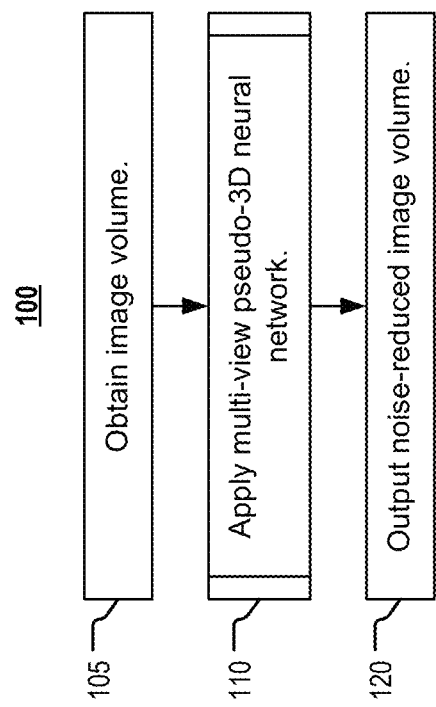
FIG. 1 is a flow diagram of a method for improving quality of a medical image volume, according to an exemplary embodiment of the present disclosure.

The terms "a" or "an", as used herein, are defined as one or more than one. The term "plurality", as used herein, is defined as two or more than two. The term "another", as used herein, is defined as at least a second or more. The terms "including" and/or "having", as used herein, are defined as comprising (i.e., open language). Reference throughout this document to "one embodiment", "certain embodiments", "an embodiment", "an implementation", "an example" or similar terms means that a particular feature, structure, or characteristic described in connection with the embodiment is included in at least one embodiment of the present disclosure. Thus, the appearances of such phrases or in various places throughout this specification are not necessarily all referring to the same embodiment. Furthermore, the particular features, structures, or characteristics may be combined in any suitable manner in one or more embodiments without limitation.

In recent years, deep learning-based methods have been proposed for improving computed tomography (CT) image quality. For image denoising, in particular, several strategies have been proposed, including residual encoder-decoder convolutional neural networks (CNNs), wavelet domain residual CNNs, perspective CNNs, K-sparse autoencoders, generative adversarial networks, multiscale CNNs, and the like. Each approach, however, has been targeted to only two-dimensional (2D) images.

When three-dimensional (3D) image volumes are considered, fewer approaches have been assessed. Transfer-learning provides one approach to accelerate denoising of 3D image volumes. However, inferencing by such techniques, though better image quality may be achieved, is impractically-slow due to the fully 3D nature of the network.

It may be helpful, when considering the case of a 3D image volume, to first consider videos, which include a spatial domain (having two spatial dimensions) and temporal domain (having one temporal dimension). For this reason, in video classification and understanding, a pseudo-3D residual network that decomposes a 3×3×3 convolution into a 1×3×3 convolution and a 3×1×1 convolution, applied to the spatial domain and to the temporal domain, respectively, can be employed. Results obtained via such a pseudo-3D approach show better performance and faster inference speed compared to fully 3D networks.

Accordingly, the present disclosure provides a pseudo-3D approach for medical image volumes, wherein each medical image volume can be considered as separate anatomical planes, or anatomical directions, having x, y, and z dimensions.

According to an embodiment, the present disclosure includes a workflow framework for a deep learning-based method that improves image quality of medical image volumes.

In an embodiment, the method includes implementation of a convolutional neural network-based structure that synergistically combines a multi-view pseudo-3D module and an improved U-net framework. The U-net framework is a multi-scale convolutional neural network framework that can efficiently learn texture information at different scale levels. The proposed multi-view pseudo-3D module is synergistically-integrated into the U-net framework.

The convolutional neural network-based structure described herein, and referred to herein as a pseudo-3D neural network (P3DNN), is trained according to a cascade weight-based loss function that improves texture extraction from each imaging volume.

According to an embodiment, the proposed cascade weight-based loss function provides a solution to handle mismatch, which may be a result of image artifacts, between input image volumes and target image volumes during training, further improving the trained network performance. Practically speaking, the cascade weight-based loss function applies different weights to different regions of input image volumes. If regions are determined to have a mismatch, relevant weights can be set to, in an example, 0. Thus, mismatched regions do not contribute to the training.

In an embodiment, the present disclosure includes a workflow framework for a deep learning-based denoising method that improves image quality of CT image volumes. This approach is advantageous as previous methods are limited by the reality that a CT image volume has different noise texture and different spatial resolutions in different slice directions. For instance, a given CT image volume will have different noise conditions when considered from a sagittal direction than when considered from a transverse direction, particularly after image reconstruction. Accordingly, the proposed multi-view pseudo-3D module of the P3DNN can enable denoising of the input image volume by improving image quality in the transverse direction, the sagittal direction, and the coronal direction. In each direction, the pseudo-3D convolution is used to learn 3D texture with faster speed than conventional 3D convolution methods.

In other words, existing 2D denoising methods can only consider denoising in one-view direction, while 3D denoising methods suffer from reduced computational speeds. Accordingly, the proposed P3DNN can improve image quality simultaneously at longitudinal (i.e., sagittal) and transverse directions while exploiting the improved U-net pseudo-3D structure to achieve the improved denoising performance with faster speed.

According to an embodiment, the P3DNN can include a training phase and an implementation phase. The training phase may be considered as offline network training while the implementation phase, in the event that noise is being considered, for instance, may be considered as online noise reduction with the trained P3DNN. During offline network training, inputs to the P3DNN and target medical image volumes may be generated from a training database. The inputs may be low-dose CT image volumes from analytical reconstruction, and the target medical image volumes may be high-dose CT image volumes generated by iterative reconstruction. The cascade weight-based loss function described above may be used for training the P3DNN. During online noise reduction with the trained P3DNN, similar methods to those applied during offline network training may be used to generate the input image volume from patient X-ray projection data and to provide the input image volume to the trained P3DNN.

While the P3DNN, with or without the cascade weight-based loss function, may be implemented for reducing noise in medical image volumes, it should be appreciated that the P3DNN can be also be generally applied, with or without the cascade weight-based loss function, to improving quality of medical image volumes. For instance, the P3DNN may be implemented for, among other types of image quality improvement, artifact reduction, segmentation, super-resolution, and scatter correction.

In an embodiment, the P3DNN, as introduced above and described in greater detail below, may be similarly implemented for artifact reduction, the P3DNN being configured to receive a CT image volume having artifacts and to generate an estimated CT image volume with the artifacts reduced. The P3DNN can be trained by providing reference CT image volumes, with real or simulated artifacts (e.g. cone-beam artifacts), as input to the P3DNN and minimizing an error between an estimated 'reduced artifact' image and a ground truth CT image volume corresponding to the reference CT image volume having real or simulated artifacts. In the case of simulated artifacts within the input, the unmodified CT image volume may be used as the ground truth CT image volume. In the case of real artifacts within the input, an iterative artifact reduction method can be applied to the reference CT image volume and the modified CT image volume may be used as the ground truth CT image volume.

In an embodiment, the P3DNN, as introduced above and described in greater detail below, may be similarly implemented for super-resolution, the P3DNN being configured to receive a CT image volume having reduced resolution and to generate an estimated higher resolution CT image volume. The P3DNN can be trained by providing low-resolution reference CT image volumes as input to the P3DNN and minimizing an error between an estimated 'high-resolution' image and a ground truth high-resolution CT image volume corresponding to the low-resolution reference CT image volume. Further, it can be appreciated that the U-net architecture can be readily implemented for super-resolution tasks.

In an embodiment, the P3DNN, as introduced above and described in greater detail below, may be similarly implemented for scatter correction, the P3DNN being configured to receive a CT image volume having scatter and to generate an estimated CT image volume with scatter corrected. The P3DNN can be trained by providing reference CT image volumes, with real or simulated scatter, as input to the P3DNN and minimizing an error between an estimated 'scatter corrected' image and a ground truth CT image volume corresponding to the reference CT image volume having real or simulated scatter. In the case of simulated scatter within the input, the unmodified CT image volume may be used as the ground truth CT image volume. In the case of real scatter within the input image, an iterative scatter correction method, such as an RTE based simulation, can be applied to the reference CT image volume and the modified CT image volume may be used as the ground truth CT image volume.

In an embodiment, the P3DNN, as introduced above and described in greater detail below, may be similarly implemented for segmentation, the P3DNN being configured to receive a CT image volume and to generate a segmented CT image volume with the target tissues, target objects, target organs, and/or target lesions identified. The P3DNN can be trained by providing reference CT image volumes as input to the P3DNN and minimizing an error between an estimated segmented image and a ground truth segmented CT image volume corresponding to the reference CT image.

Referring now to the Drawings, FIG. 1 provides a flow diagram of a method for reducing noise in a medical image volume, according to an exemplary embodiment of the present disclosure. While the remainder of the disclosure focuses on noise reduction, it can be appreciated that other types of image quality improvement may be readily achieved using similar methods to those described herein.

At step 105 of method 100, an image volume can be obtained. In an embodiment, the image volume is obtained from a CT scanner. The image volume may be an image volume reconstructed from X-ray projection data corresponding to a region of an object. The object may be a body of a patient. In an embodiment, the X-ray projection data may be obtained via low-dose radiation in order to reduce radiation exposure to, for instance, the patient. The image reconstruction of the X-ray projection data corresponding to the region of the body of the patient may be an analytical reconstruction or similar method. In an example, the image reconstruction of the X-ray projection data corresponding to the region of the body of the patient is an analytical reconstruction by filtered backprojection. Generally, it can be appreciated that the image reconstruction performed for the image volume obtained at step 105 of method 100 is not intended to result in, in and of itself, a clinically relevant image volume.

At sub process 110 of method 100, a multi-view pseudo-3D neural network, according to the present disclosure, can be applied to the image volume. The P3DNN, as will be described in detail with reference to the remaining figures, includes one or more implementations of a multi-view pseudo-3D (MVP3D) module.

As will be described, the MVP3D module is configured to split the obtained image volume into three image volumes corresponding to the three anatomical views (or three anatomical directions) of the patient. These three anatomical views of the patient, which include a sagittal view, a coronal view, and a transverse view, as would be understood by one of ordinary skill in the art, provide the ability to evaluate the obtained image volume from multiple perspectives. After splitting the obtained image volume, each anatomical image volume can be processed according to at least one convolution. In an example, the at least one convolution can be two convolutions that utilize a step-wise approach. The step-wise approach can include serial application of, to each anatomical image volume, a n×n×1 convolutional kernel and a 1×1×n convolution kernel, where n is an integer. Following processing of each anatomical image volume, the results can be concatenated and output to a subsequent step of the P3DNN.

In an embodiment, the P3DNN is configured to implement the MVP3D module in addition to a number of additional layers of the P3DNN that sub sample, pool, upsample, inverse sub sample, sum, convolve, and the like. The network architecture of the P3DNN will be described in greater detail with reference to subsequent figures.

An estimated image volume generated by the P3DNN can then be provided to step 120 of method 100. In an embodiment, the output image volume at step 120 of method 100 is based on a training phase of the P3DNN, wherein a high-dose image volume is used as a reference, or target. Accordingly, the image volume estimated by the P3DNN is output as a clinically-relevant output image volume.

In an embodiment, the P3DNN is configured to receive an input image volume obtained via low-dose radiation and to generate an output image volume that estimates a high-dose radiation acquisition with reduced noise. This can be better appreciated with reference to the training phase for the P3DNN, but should remain front of mind as a solution to reducing radiation exposure to the patient while generating clinically-relevant imaging volumes.

Figure 2:
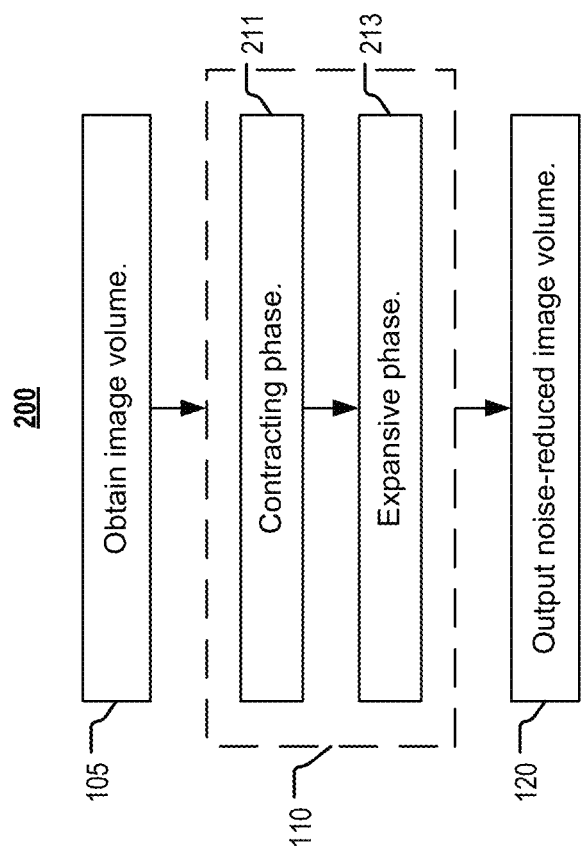
FIG. 2 is a flow diagram of a method for improving quality of a medical image volume, according to an exemplary embodiment of the present disclosure.

With reference now to FIG. 2, a flow diagram of a method for reducing noise in a medical image volume, according to an exemplary embodiment of the present disclosure, will be described.

At step 105 of method 200, an image volume can be obtained. In an embodiment, the image volume is obtained from a CT scanner. The image volume may be an image volume reconstructed from X-ray projection data corresponding to a region of a body of a patient (i.e., a 3D region of the body of the patient). In an embodiment, the X-ray projection data may be obtained via low-dose radiation in order to reduce radiation exposure to the patient. The image reconstruction of the X-ray projection data corresponding to the region of the body of the patient may be an analytical reconstruction. In an example, the image reconstruction of the X-ray projection data corresponding to the region of the body of the patient is an analytical reconstruction by filtered backprojection. Generally, it can be appreciated that the image reconstruction performed for the image volume obtained at step 105 of method 200 is not intended to result in, in and of itself, a clinically-relevant image volume.

At sub process 110 of method 200, a multi-view pseudo-3D neural network, or the P3DNN of the present disclosure, can be applied to the image volume. The P3DNN includes one or more implementations of a multi-view pseudo-3D (MVP3D) module arranged within a U-net architecture.

In particular, the P3DNN, as applied to the image volume at sub process 110 of method 200, may include a contracting phase 211 and an expansive phase 213. The contracting phase 211 and the expansive phase 213, and layers therein, can be better appreciated visually with reference to FIG. 4, which will be described in detail later.

During each of the contracting phase 211 and the expansive phase 213, two or more instances of the MVP3D may be applied to the image volume, or processed versions thereof. In addition, each of the contracting phase 211 and the expansive phase 213 may include complementary layers of the P3DNN. The complementary layers may include activation layers, sub sampling layers, pooling layers, upsampling layers, concatenating layers, inverse sub sampling layers, convolution layers, and summation layers, among others.

In an embodiment, the MVP3D module is configured to split the obtained image volume, or another intermediate input volume, into three image volumes corresponding to the three anatomical views of the patient. The three image volumes may be referred to interchangeably herein as each of a plurality of 3D image datasets. The three anatomical views of the patient, which include a sagittal view, a coronal view, and a transverse view, as would be understood by one of ordinary skill in the art, provide the ability to evaluate the obtained image volume from multiple perspectives. After splitting the obtained image volume into each of a sagittal image volume, a transverse image volume, and a coronal image volume, each anatomical image volume (e.g. a sagittal plane dataset, a transverse plane dataset, and a coronal plane dataset) can be processed according to at least one convolution. In an embodiment, as in the MVP3D module, the at least one convolution can be two convolutions that utilize a step-wise, serial approach. The step-wise, serial approach can include application of, to each anatomical image volume, a n×n×1 convolutional kernel and a 1×1×n convolution kernel, where n is an integer based on the determined filter size. Following processing of each anatomical image volume by the two convolution filters, the results can be concatenated and output to a subsequent step of the P3DNN.

Following application of the P3DNN at sub process 110 of method 200, a clinically-relevant estimated medical image volume can be generated and provided to step 120 of method 200. The estimated medical volume can be an estimation of a high-dose medical image volume with reduced noise. Accordingly, at step 120 of method 200, the estimated image volume can be output for diagnostic evaluation.

Figure 3A:
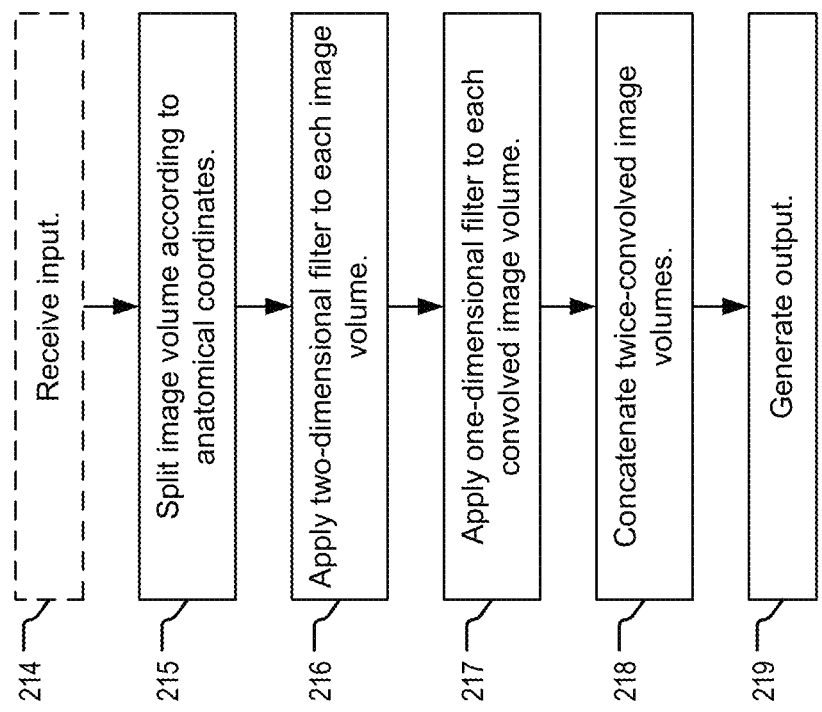
FIG. 3A is a flow diagram of a sub process of a method for improving quality of a medical image volume, according to an exemplary embodiment of the present disclosure.
Figure 3B:
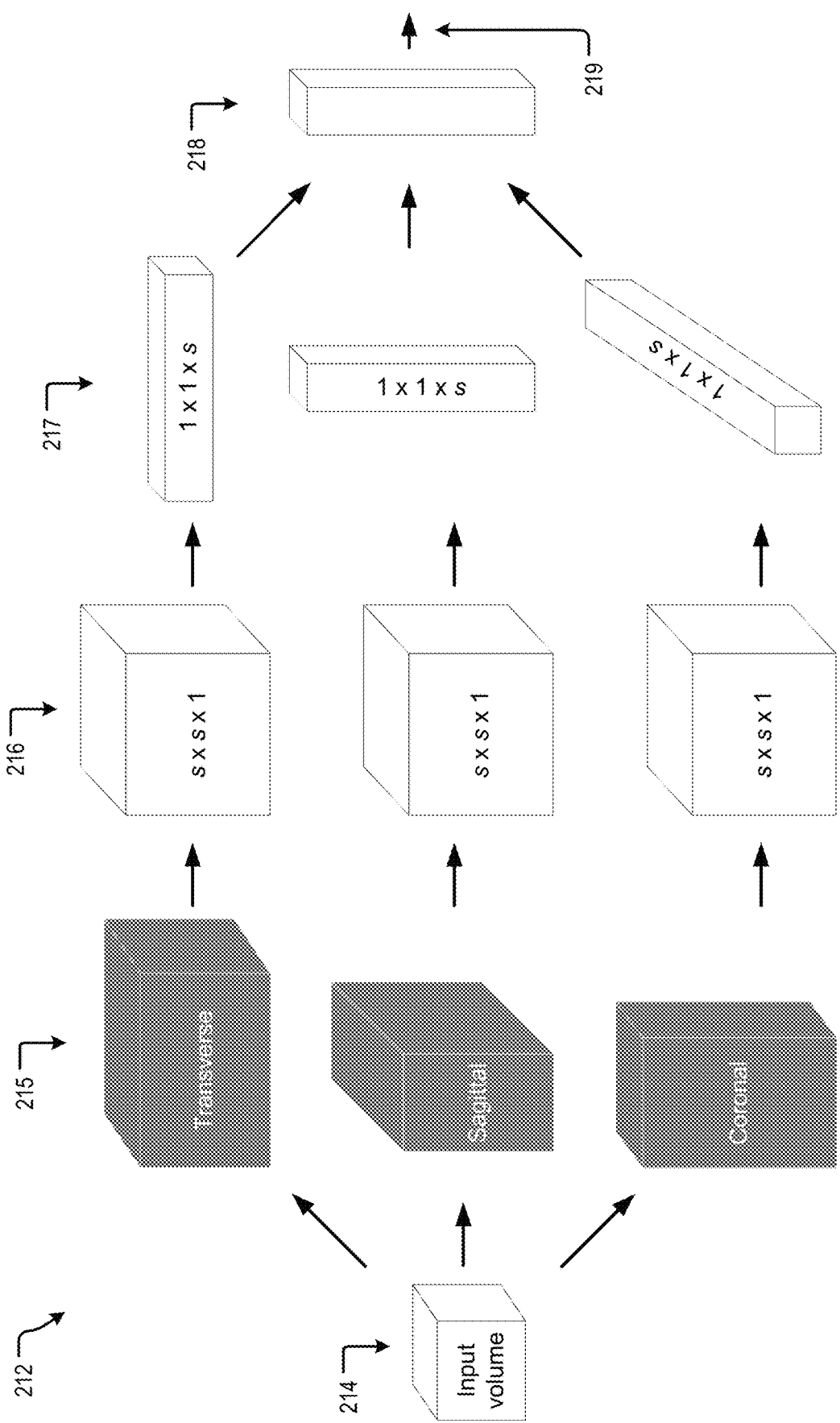
FIG. 3B is a schematic of a sub process of a method for improving quality of a medical image volume, according to an exemplary embodiment of the present disclosure.

With reference now to FIG. 3A and FIG. 3B, a low-level flow diagram of the MVP3D module, referred to in FIG. 3A and FIG. 3B as 212, will be described.

The MVP3D module is implemented in response to an understanding that CT image volumes, in particular, have different noise texture and spatial resolution in different directions. Thus, implementation of the MVP3D module within the P3DNN allows for denoising an input CT image volume and improving image quality in the transverse direction, sagittal direction, and coronal direction.

At step 214, an input can be received. Appreciating that the MVP3D module 212 can be implemented during the contracting phase of the P3DNN and the expansive phase of the P3DNN, the received input can be an image volume obtained from a CT scanner or a processed version of the image volume.

In any event, the received input can be provided to step 215, wherein the received input can be split into three image volumes corresponding to the three anatomical views of the patient (e.g. sagittal image volume, transverse image volume, coronal image volume). As can be appreciated, each image volume corresponding to a respective anatomical view of the patient can comprise three dimensions, with a third dimension being a depth dimension corresponding to a number of 'slices' in that given anatomical direction. Moreover, though referred to herein as anatomical directions, it can be appreciated that any three orthogonal directions may be considered for this task, anatomical directions merely being widely understood, readily applicable, and relevant to CT image acquisition.

After splitting the obtained image volume into each of a sagittal image volume, a transverse image volume, and a coronal image volume, each anatomical image volume can be processed according to at least one convolution. In an embodiment, the MVP3D module 212 includes at least two convolutions. In an example, the at least two convolutions are applied sequentially.

At step 216, a first convolution can be applied to each anatomical image volume. The first convolution can include applying a n×n×1 convolutional kernel to each anatomical image volume, where n is an integer based on the determined filter size.

At step 217, a second convolution can be applied to the convolved image volume generated at step 216. The second convolution can include applying a 1×1×n convolution kernel to each convolved anatomical image volume, where n is an integer.

In an example, the first convolution kernel is a 3×3×1 filter and the second convolution kernel is a 1×1×3 filter. In this way, the two kinds of filters can directly influence each other in the same path while only the 1×1×3 filter is directly connected to the final output of the MVP3D module 212. As a result, instead of applying a single 3×3×3 filter, the convolution problem is reduced to a series of 2D convolution problems that are more computationally practical.

Following processing of each anatomical image volume by the two convolutional filters, the resulting twice-convolved image volumes can be concatenated at step 218. An output can be generated at step 219 based on the concatenated results of step 218. In an embodiment, the generated output can be provided to a subsequent layer of the P3DNN. In an example, the subsequent layer may be an additional MVP3D module. In another example, wherein the subsequent layer is a layer within the contracting phase of the P3DNN, the subsequent layer may be a pooling layer. In another example, wherein the subsequent layer is a layer within the expansive phase of the P3DNN, the subsequent layer may be an upsampling layer.

Figure 4:
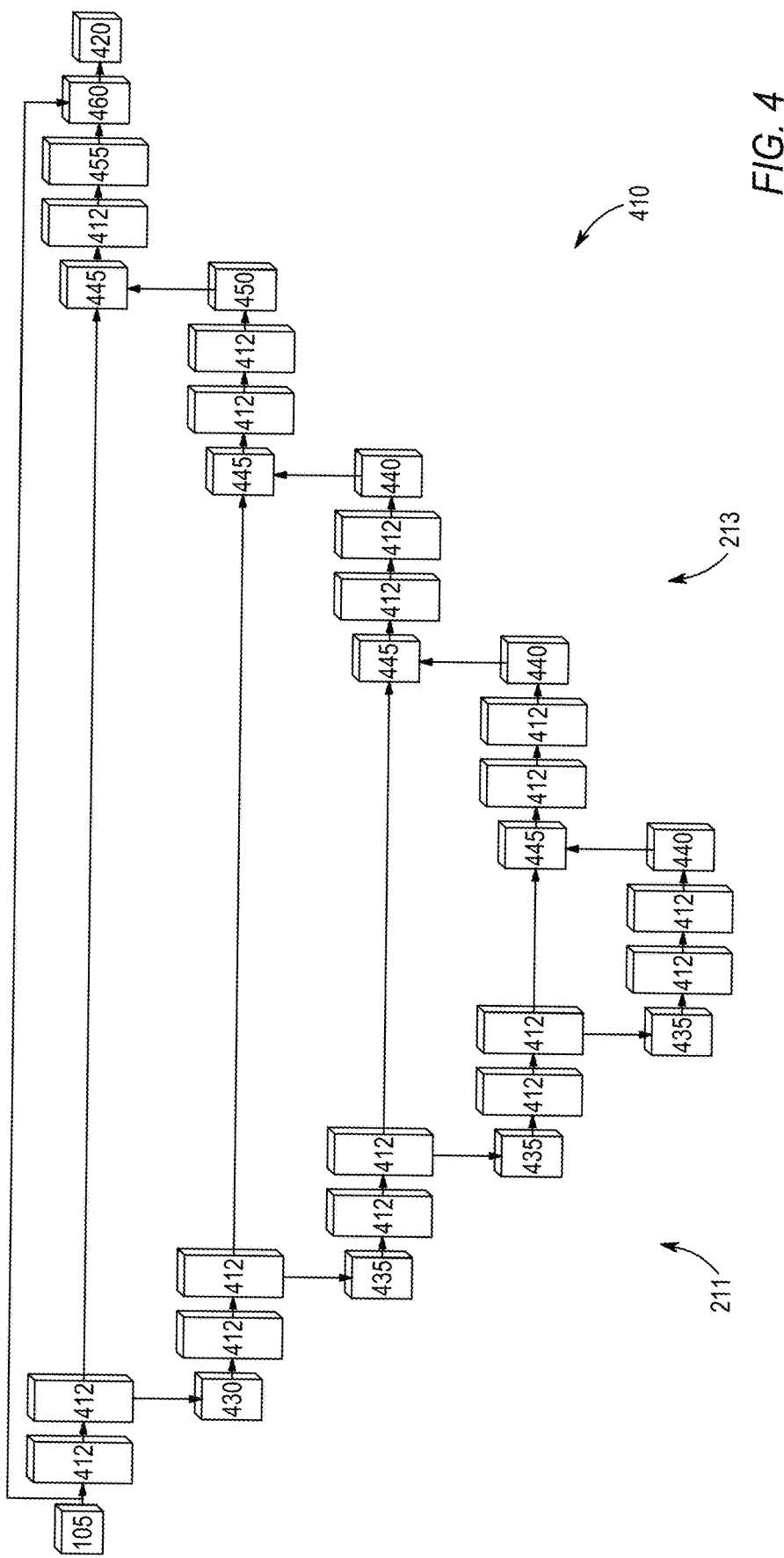
FIG. 4 is a schematic of a pseudo-three-dimensional neural network, according to an exemplary embodiment of the present disclosure.

Referring now to FIG. 4, an exemplary architecture of a P3DNN 410 will be described. Visually, it can be appreciated that the P3DNN 410 is based on a U-net architecture that is symmetric and consists of two major parts—a left side that is called a contracting phase 211 and a right side that is called an expansive phase 213. In effect, the contracting phase 211 is a convolutional process while the expansive phase 213 is a transposed convolutional process.

To start, an input image volume 105 is provided as an input layer to the contracting phase 211 of the P3DNN 410. First, an MVP3D module 412 can be applied sequentially. A sub sampling layer 430 followed by two instances of the MVP3D module 412 can then be applied. The sub sampling layer 430 includes feature maps having M * N * C, where M and N are dimensions of feature maps, C is the number of feature maps, and a related matrix operation may be $$\left(\frac{M}{2} * \frac{N}{2} * 4C\right).$$

In this way, the sub sampling layer 430 allows for the retention of more features as compared with a pooling layer. Next, a contracting sub process of pooling 435 followed by two instances of the MVP3D module 412 can then be applied. The contracting sub process can be performed three times, at which point the 'bottom' of the P3DNN 410 has been reached. At this point, instead of continuing the convolution approach by applying a pooling layer, a transposed convolution approach of the expansive phase 213 is begun by applying an upsampling layer 440. Subsequently, an expansive sub process including a concatenating layer 445 followed by two instances of the MVP3D module 412 and, ultimately, an upsampling layer 440, can be applied. The expansive sub process is performed twice during the expansive phase 213. Next, an output of the second iteration of the expansive sub process is provided to a concatenating layer 445 followed by two instances of the MVP3D module 412. With the expansive phase 213 nearly complete, the output of the second instance of the MVP3D module 412 is then provided to an inverse sub sampling layer 450. The inverse sub sampling layer 450 includes provides an alternative matrix operation to that of the sub sampling layer 430 during the contracting phase 211 in order to return the matrix dimension to M * N * C. The output of the inverse sub sampling layer 450 is then provided to a concatenating layer 445 followed by an instance of the MVP3D module 412, a convolutional layer 455 configured to adjust the dimension of the output to match the input, and a summation layer 460. An output of the summation layer 460 corresponds to an output image volume 420, or estimation of a high-dose image volume by the P3DNN 410.

In an embodiment, the P3DNN 410 of FIG. 4 can be trained according to a cascade weight-based loss function.

Figure 5:
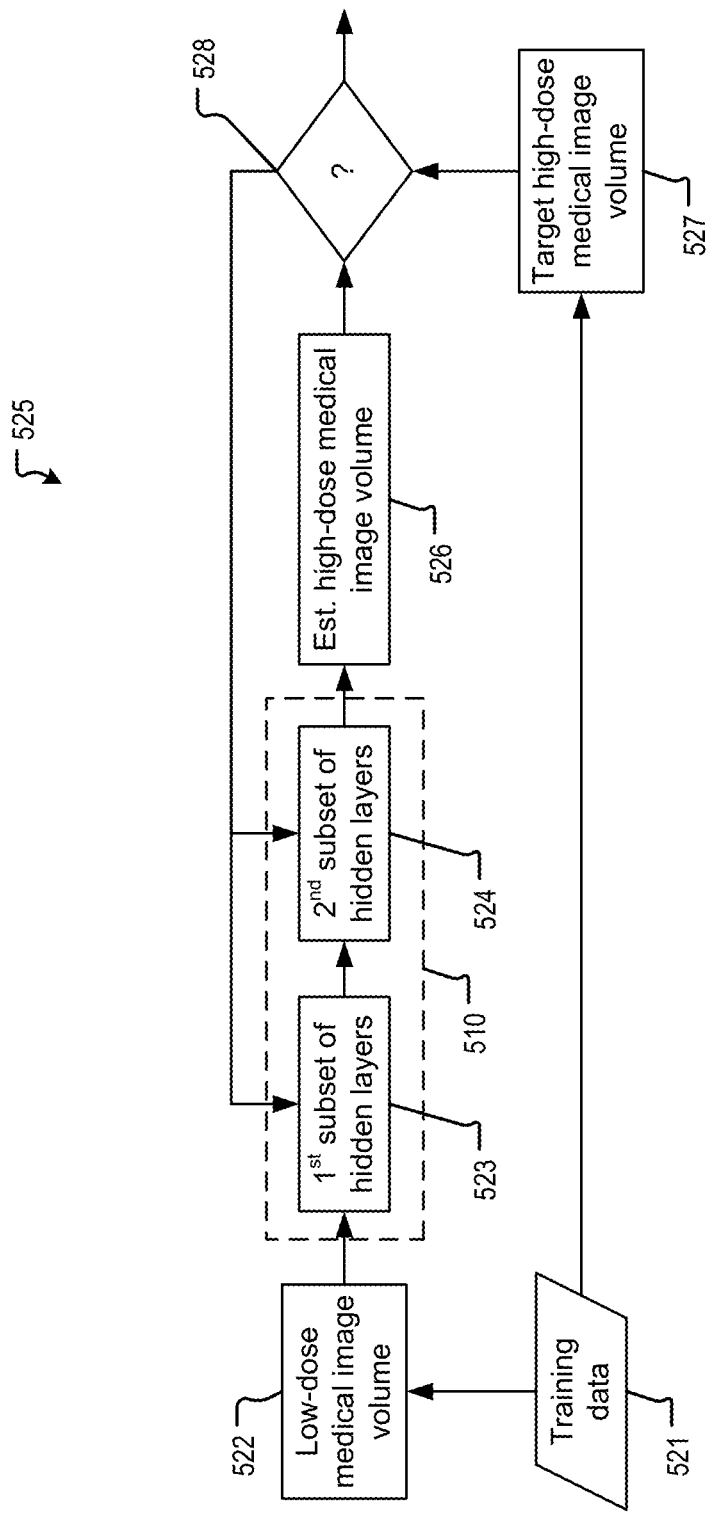
FIG. 5 is a flow diagram of a training phase of a method for improving quality of medical image volumes, according to an exemplary embodiment of the present disclosure.

To this end, FIG. 5 is a flow diagram of a training phase of a method for reducing noise in a medical image volume, according to an exemplary embodiment of the present disclosure. The training phase may include optimization of a neural network, which can vary with application and can include residual networks, convolutional neural networks, encoder/decoder networks, and the like. In an exemplary embodiment, the method of the present disclosure employs a P3DNN, as described above with reference to FIG. 4.

Generally, the P3DNN receives training data, or, for instance, training image volumes, as inputs and outputs an estimated image volume that is minimized relative to a reference image volume. In an instance, the training image volume may be a low-dose medical image volume and the estimated image volume may be an approximation of the reference image volume (e.g., a corresponding high-dose medical image volume). In an embodiment, the low-dose medical image volume may be generated by analytical reconstruction. The reference image volume may be an image volume based on data acquired from a high-dose acquisition, model-based reference, or a ground-truth profile (generated via model-based approach). In an embodiment, the reference image volume is reconstructed by an iterative reconstruction.

Specifically, training a P3DNN 510 begins with obtaining the training data from a training database 521. The training data can include a low-dose medical image volume 522 and a corresponding target high-dose medical image volume 527. The low-dose medical image volume 522 can be provided as an input layer of the P3DNN 510 at step 523. The input layer can be provided to a first subset of hidden layers of the P3DNN 510 at step 523. In the event the architecture of the P3DNN 510 follows that of FIG. 4, the first subset of hidden layers of the P3DNN 510 may be a contracting phase of the P3DNN 510. In an embodiment, the contracting phase of the P3DNN 510 may include the MVP3D module described with respect to FIG. 3A and FIG. 3B. In an embodiment, the contracting phase of the P3DNN 510 can include convolutional layers, concatenation layers, sub sampling layers, pooling layers, batch normalization layers, and activation layers, among others. The activation layers may employ a rectified linear unit (ReLU). In an embodiment, an output of the first subset of hidden layers is then the input for a second subset of hidden layers of the P3DNN 510, at step 524, during an expansive phase. In an embodiment, the expansive phase of the P3DNN 510 may include the MVP3D module described with respect to FIG. 3A and FIG. 3B. In an embodiment, the expansive phase of the P3DNN 510 can include convolutional layers, concatenation layers, upsampling layers, inverse sub sampling layers, and summation layers, among others. Subsequent n hidden layers of the P3DNN 510, or subsequent n subsets of hidden layers of the P3DNN 510, can be included, as desired. As in the example of FIG. 5, the output of the second subset of hidden layers at step 524 of training phase 525 then becomes the input for an output layer at step 526, the output layer at step 526 being a fully connected layer and describing an estimated high-dose medical image volume based on the training data. The P3DNN 510 estimated high-dose image volume can then be compared with the corresponding target high-dose medical image volume 527 at step 528, and a loss function therebetween can be minimized. If, at step 528, it is determined that an error criterion is met and the loss function has been minimized, the P3DNN 510 is determined to be sufficiently trained and ready for implementation with unknown, real-time data. Alternatively, if it is determined at step 528 that the error criterion is not met and the loss function has not been minimized, the training phase 525 returns to step 523 and updates are made to weights/coefficients of the P3DNN 510.

According to an embodiment, as implemented at step 528 of FIG. 5, the loss function can be defined as a minimization function relating the P3DNN-estimated medical image volume ($f_{net}(MIV_{input})$) and the target high-dose medical image volume ($MIV_{target}$). In other words, $$\underset{f_{net}}{\text{argmin}} \| W \cdot (f_{net}(MIV_{input}) - MIV_{target}) \|_p$$

where $f_{net}$ is the P3DNN to be trained, $MIV_{input}$ is the input medical image volume, $f_{net}(MIV_{input})$ is the P3DNN-estimated high-dose medical image volume, $MIV_{target}$ is the target high-dose medical image volume, $\| \ \|_p$ is the p-norm for minimization, and W are weights. In an embodiment, and as will be described later with respect to FIG. 6A and FIG. 6B, W may consider the mismatch between $MIV_{input}$ and $MIV_{target}$ and may define cascaded weights as $$W = W_{mo} W_{ma} W_{Hub}$$

where $W_{mo}$ is a motion-based weight, $W_{ma}$ is a metal artifact-based weight, and $W_{HUb}$ is a Hounsfield Unit (HU)-based weight that encompasses HU bias via, for example, thresholding. In considering the mismatch between an input medical image volume ($MIV_{input}$) and a target medical image volume ($MIV_{target}$), the cascade weight-based loss function may apply different weights to different regions of the input image volume based on a determined degree of mismatch with the target medical image volume. For instance, a region of an input image volume that is substantially mismatched with a target medical image volume may be given a lower weight (e.g., 0, 1, . . . , x), for the purposes of training, as compared to a region of the input medical image volume that is substantially matched with the target medical image volume. In an example, the loss function can be minimized using classic deep learning optimization methods, such as stochastic gradient descent, among others. The above-described loss function will be described with detail in a later section.

Figure 6A:
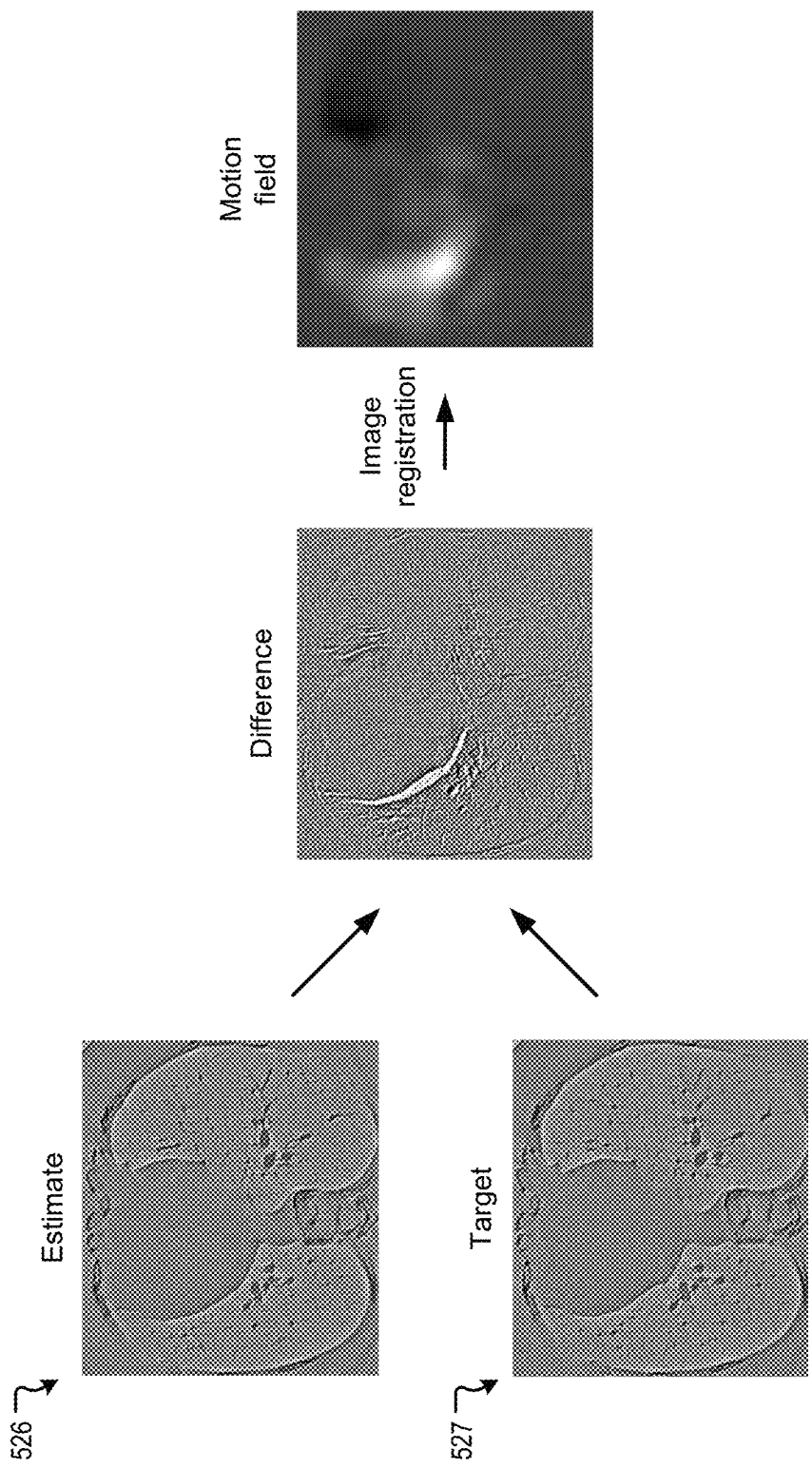
FIG. 6A is a graphical illustration of a sub process for determining weights of a parameter of a loss function, according to an exemplary embodiment of the present disclosure.

With respect to FIG. 6A and FIG. 6B, it can be appreciated that medical image quality may be impacted by several factors including, for example, patient respiration, patient heartbeat, metal implantations within the patient, radiation dose of the scan, and the like. Further, the mere selection of one of a variety of image reconstruction techniques can greatly impact the ability to generate clinically relevant images. The use of a cascaded weight within the loss function accounts for differences, caused by these factors and others, between an input medical volume and a target high-dose medical image volume during optimization of the P3DNN.

As it relates to FIG. 6A, artifacts associated with patient motion can be addressed by calculating a motion weight ($W_{mo}$) as a component of the cascaded weight (W). To this end, the motion weight can be calculated using image registration between the input medical image volume 526 and the target high-dose medical image volume 527. The difference can be used to generate a motion field via image registration, and the motion field can be used to calculated the motion weight, $W_{mo}$, where $$W_{mo} = \frac{1}{1 + |M_v|^n}$$

where n is a fixed integer, such as 1 or 2, and is based on a consistency between the input medical image volume and the target medical image volume. In this way, the motion weight is a function of the estimated motion between the input medical image volume 526 and the target high-dose medical image volume 527. Practically speaking, when the estimated motion is large, a smaller value will be assigned to the motion weight, ($W_{mo}$). In an embodiment, the motion weight can be calculated for different regions within the input medical image volume 526.

With reference now to FIG. 6B, artifacts associated with metal implantations within the patient can be addressed by calculating a metal artifact-based weight, $W_{ma}$. To this end, the metal artifact-based weight can be calculated by summing or concatenating a metal mask ($M_m$) and a streaks mask ($M_s$). The metal mask can be calculated by applying a HU thresholding method, or other relevant method, to an input medical image volume 526. A segmentation of the input medical image volume 526, based on the metal mask, is shown in FIG. 6B. The streaks mask can be calculated by, in one embodiment, comparing the input medical image volume 526 to the target high-dose medical image volume. To calculate the metal artifact-based weight, $W_{ma}$, the metal mask and the streaks mask can be summed as $$W_{ma} = \frac{1}{1 + (|M_m| + |M_s|)^n}$$

or concatenated as $$W_{ma} = \frac{1}{1 + (|M_m| \cdot |M_s|)^n}$$

where n is an integer such as 1 or 2. In an embodiment, the metal artifact-based weight can be calculated for different regions within the input medical image volume 526

Figure 7:
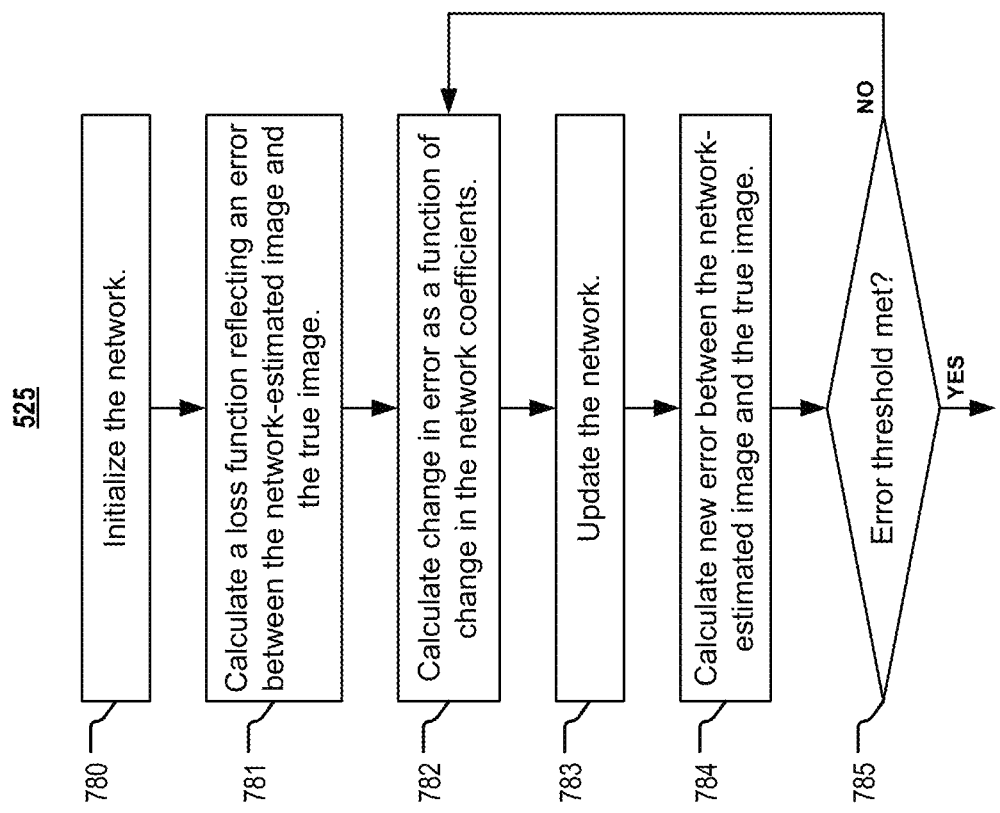
FIG. 7 is a flow diagram of neural network training of a training phase of a method for improving quality of a medical image volume, according to an exemplary embodiment of the present disclosure.

Now, a more detailed description of FIG. 5 is provided with respect to FIG. 7 through FIG. 10B. This description can be generalized, as would be understood by one of ordinary skill in the art. FIG. 7 shows a flow diagram of one implementation of the training phase performed during optimization of the P3DNN.

During the training phase, representative data from the training data database are used as training data to train a P3DNN, resulting in an optimized P3DNN being output from the training phase. The term "data" here can refer to an image of the training image database. More generally, data can be referred to as defect-exhibiting data, for which the "defect" can be any undesirable characteristic that can be affected through image acquisition (e.g. motion) or image processing (e.g., noise or an artifact). In an example using training images for data, the training phase of FIG. 5 can be an offline training method that trains the P3DNN using a large number of low-dose training image volumes that are paired with corresponding high-dose training image volumes to train the P3DNN to estimate a high-dose image volume from the low-dose training image volumes.

During the training phase, a training database is accessed to obtain a plurality of datasets and the network is iteratively updated to reduce the error (e.g., the value produced by a loss function), wherein updating the network includes iteratively updating values of, for example, network coefficients, at each layer of the P3DNN, such that the low-dose data processed by the P3DNN, increasingly, closely matches the target high-dose medical image volume. In other words, P3DNN infers the mapping implied by the training data, and the loss function, or cost function, produces an error value related to the mismatch between the target high-dose medical image volume and the medical image volume estimated by the current iteration of the P3DNN. For example, in certain implementations, the loss function can use the mean-square error to minimize the average squared error. In the case of a multilayer perceptron (MLP) neural network, the backpropagation algorithm can be used for training the network by minimizing the mean-square-error-based loss function using a (stochastic) gradient descent method. A more-detailed discussion of updating of network coefficients can be found below with reference to FIG. 7.

Training a neural network model essentially means selecting one model from the set of allowed models (or, in a Bayesian framework, determining a distribution over the set of allowed models) that minimizes the cost criterion (i.e., the error value calculated using the cost function). Generally, the P3DNN can be trained using any of numerous algorithms for training neural network models (e.g., by applying optimization theory and statistical estimation).

For example, the optimization method used in training the P3DNN can use a form of gradient descent incorporating backpropagation to compute the actual gradients. This is done by taking the derivative of the cost function with respect to the network parameters and then changing those parameters in a gradient-related direction. The backpropagation training algorithm can be: a steepest descent method (e.g., with variable learning rate, with variable learning rate and momentum, and resilient backpropagation), a quasi-Newton method (e.g., Broyden-Fletcher-Goldfarb-Shanno, one step secant, and Levenberg-Marquardt), or a conjugate gradient method (e.g., Fletcher-Reeves update, Polak-Ribiére update, Powell-Beale restart, and scaled conjugate gradient). Additionally, evolutionary methods, such as gene expression programming, simulated annealing, expectation-maximization, non-parametric methods and particle swarm optimization, can also be used for training the P3DNN.

With reference again to FIG. 7, the flow diagram is a non-limiting example of an implementation of the training phase 525 for training the P3DNN using the training data. The data in the training data can be from any of the training datasets, comprising a plurality of image volumes, within the training database.

At step 780 of training phase 525, an initial guess is generated for the coefficients of the P3DNN. For example, the initial guess can be based on a priori knowledge of the region being imaged or one or more exemplary denoising methods, edge-detection methods, and/or blob detection methods. Additionally, the initial guess can be based on one of the LeCun initialization, an Xavier initialization, and a Kaiming initialization.

Step 781 to step 785 provide a non-limiting example of an optimization method for training the P3DNN. In step 781 of training phase 525, an error is calculated (e.g., using a loss function/cost function) to represent a measure of the difference (e.g., a distance measure) between the target high-dose medical image volume (i.e., reference medical image volume ground truth) and the output data of the P3DNN as applied in a current iteration of the P3DNN. The error can be calculated using any known cost function or distance measure between the image data, including those cost functions described above. Further, in certain implementations the error/loss function can be calculated using one or more of a hinge loss and a cross-entropy loss. In an example, as described above, the loss function can be defined as a minimization function relating the P3DNN-estimated medical image volume ($f_{net}(MIV_{input})$) and the target high-dose medical image volume ($MIV_{target}$). In other words, $$\operatorname*{argmin}_{f_{net}} \|W \cdot (f_{net}(MIV_{input}) - MIV_{target})\|_p$$

where $f_{net}$ is the P3DNN to be trained, $MIV_{input}$ is the input medical image volume, $f_{net}(MIV_{input})$ is the P3DNN-estimated high-dose medical image volume, $MIV_{target}$ is the target high-dose medical image volume, $\| \|_p$ is the p-norm for minimization, and W are weights. As described above, this loss can be minimized using optimization methods including, among others, stochastic gradient descent.

Additionally, the loss function can be combined with a regularization approach to avoid overfitting the network to the particular instances represented in the training data. Regularization can help to prevent overfitting in machine learning problems. If trained too long, and assuming the model has enough representational power, the network will learn the noise specific to that dataset, which is referred to as overfitting. In case of overfitting, the P3DNN becomes a poor generalization, and the variance will be large because the noise varies between datasets. The minimum total error occurs when the sum of bias and variance are minimal. Accordingly, it is desirable to reach a local minimum that explains the data in the simplest possible way to maximize the likelihood that the trained network represents a general solution, rather than a solution particular to the noise in the training data. This goal can be achieved by, for example, early stopping, weight regularization, lasso regularization, ridge regularization, or elastic net regularization.

In certain implements, the P3DNN is trained using backpropagation. Backpropagation can be used for training neural networks and is used in conjunction with gradient descent optimization methods. During a forward pass, the algorithm computes the network's predictions based on the current parameters$\Theta$. These predictions are then input into the loss function, by which they are compared to the corresponding ground truth labels. During the backward pass, the model computes the gradient of the loss function with respect to the current parameters, after which the parameters are updated by taking a step size of a predefined size in the direction of minimized loss (e.g., in accelerated methods, such that the Nesterov momentum method and various adaptive methods, the step size can be selected to more quickly converge to optimize the loss function.)

The optimization method by which the backprojection is performed can use one or more of gradient descent, batch gradient descent, stochastic gradient descent, and mini-batch stochastic gradient descent. Additionally, the optimization method can be accelerated using one or more momentum update techniques in the optimization approach that results in faster convergence rates of stochastic gradient descent in deep networks, including, e.g., Nesterov momentum technique or an adaptive method, such as Adagrad sub-gradient method, an Adadelta or RMSProp parameter update variation of the Adagrad method, and an Adam adaptive optimization technique. The optimization method can also apply a second order method by incorporating the Jacobian matrix into the update step.

The forward and backward passes can be performed incrementally through the respective layers of the network. In the forward pass, the execution starts by feeding the inputs through the first layer, thus creating the output activations for the subsequent layer. This process is repeated until the loss function at the last layer is reached. During the backward pass, the last layer computes the gradients with respect to its own learnable parameters (if any) and also with respect to its own input, which serves as the upstream derivatives for the previous layer. This process is repeated until the input layer is reached.

Returning to the non-limiting example shown in FIG. 7, step 782 of the training phase 525 determines a change in the error as a function of the change in the network can be calculated (e.g., an error gradient) and this change in the error can be used to select a direction and step size for a subsequent change in the weights/coefficients of the P3DNN. Calculating the gradient of the error in this manner is consistent with certain implementations of a gradient descent optimization method. In certain other implementations, this step can be omitted and/or substituted with another step in accordance with another optimization algorithm (e.g., a non-gradient descent optimization algorithm like simulated annealing or a genetic algorithm), as would be understood by one of ordinary skill in the art.

In step 783 of the training phase 525, a new set of coefficients are determined for the P3DNN. For example, the weights/coefficients can be updated using the change calculated in step 782, as in a gradient descent optimization method or an over-relaxation acceleration method.

In step 784 of the training phase 525, a new error value is calculated using the updated weights/coefficients of the P3DNN.

In step 785 of the training phase 525, predefined stopping criteria are used to determine whether the training of the network is complete. For example, the predefined stopping criteria can evaluate whether the new error and/or the total number of iterations performed exceed predefined values. For example, the stopping criteria can be satisfied if either the new error falls below a predefined threshold or if a maximum number of iterations are reached. When the stopping criteria is not satisfied, the training phase 525 will continue back to the start of the iterative loop by returning and repeating step 782 using the new weights and coefficients (the iterative loop includes steps 782, 783, 784, and 785). When the stopping criteria are satisfied, the training phase 525 is completed.

FIG. 8 and FIG. 9 show flow diagrams of implementations of neural networks, aspects of which may be incorporated into the training phase and/or the run time phase of the P3DNN the present disclosure. FIG. 8 is general for any type of layer in a feedforward artificial neural network (ANN), including, for example, fully connected layers. FIG. 9 is specific to convolutional layers, pooling layers, batch normalization layers, and ReLU layers in a CNN. The P3DNN can include aspects of the flow diagrams of FIG. 8 and FIG. 9, including fully connected layers, convolutional layers, pooling layers, batch normalization layers, and ReLU layers, as would be understood by one of ordinary skill in the art. It should be appreciated that the descriptions related to FIG. 8 and FIG. 9 are specific to only one anatomical direction of the P3DNN of the present disclosure. For instance, it can be considered that FIG. 8 and FIG. 9 are described with reference to a sagittal image volume.

In step 887 of training phase 525, the weights/coefficients corresponding to the connections between neurons (i.e., nodes) are applied to the respective inputs corresponding to, for example, the pixels of the training image volume.

In step 888, the weighted inputs are summed. When the only non-zero weights/coefficients connecting to a given neuron on the next layer are regionally localized in an image represented in the previous layer, the combination of step 887 and step 888 is essentially identical to performing a convolution operation.

In step 889, respective thresholds are applied to the weighted sums of the respective neurons.

In sub process 890, the steps of weighting, summing, and thresholding are repeated for each of the subsequent layers.

FIG. 9 shows a flow diagram of another implementation of the P3DNN. The implementation of the P3DNN shown in FIG. 9 corresponds to operating on the training image volume at a hidden layer using a non-limiting implementation of the P3DNN.

In step 991, the calculations for a convolution layer are performed as discussed in the foregoing and in accordance with the understanding of convolution layers of one of ordinary skill in the art.

In step 992, following convolution, batch normalization can be performed to control for variation in the output of the previous layer, as would be understood by one of ordinary skill in the art.

In step 993, following batch normalization, activation is performed according to the foregoing description of activation and in accordance with the understanding of activation of one of ordinary skill in the art. In an example, the activation function is a rectified activation function or, for example, a ReLU, as discussed above.

In another implementation, the ReLU layer of step 993 may be performed prior to the batch normalization layer of step 892.

In step 994, the outputs from the convolution layer, following batch normalization and activation, are the inputs into a pooling layer that is performed according to the foregoing description of pooling layers and in accordance with the understanding of pooling layers of one of ordinary skill in the art.

In process 995, the steps of a convolution layer, pooling layer, batch normalization layer, and ReLU layer can be repeated in whole or in part for a predefined number of layers. Following (or intermixed with) the above-described layers, the output from the ReLU layer can be fed to a predefined number of ANN layers that are performed according to the description provided for the ANN layers in FIG. 8. The final output will be an estimation of a high-dose medical image volume.

Figure 10A:
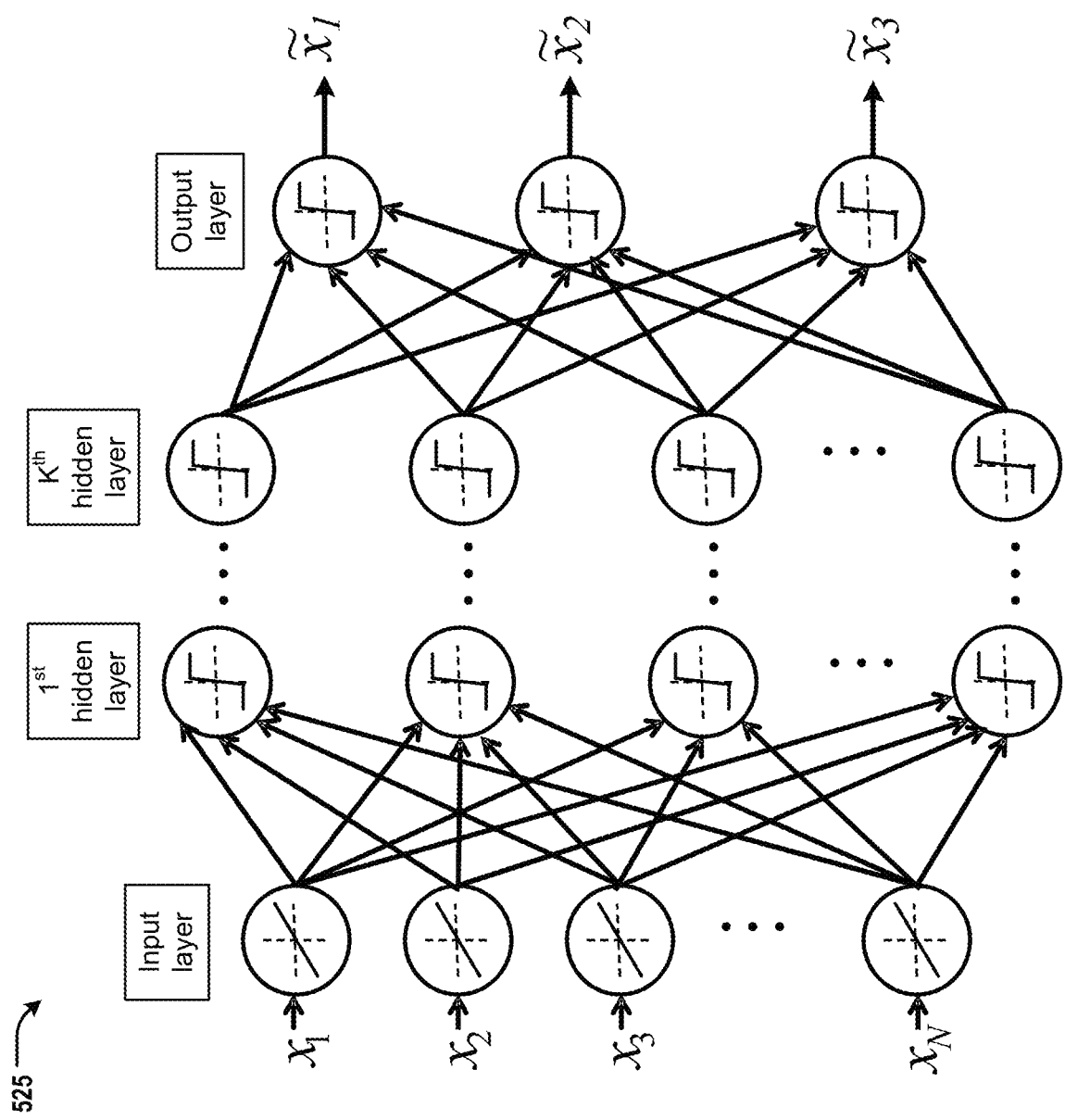
FIG. 10A is an example of a feedforward artificial neural network.
Figure 10B:
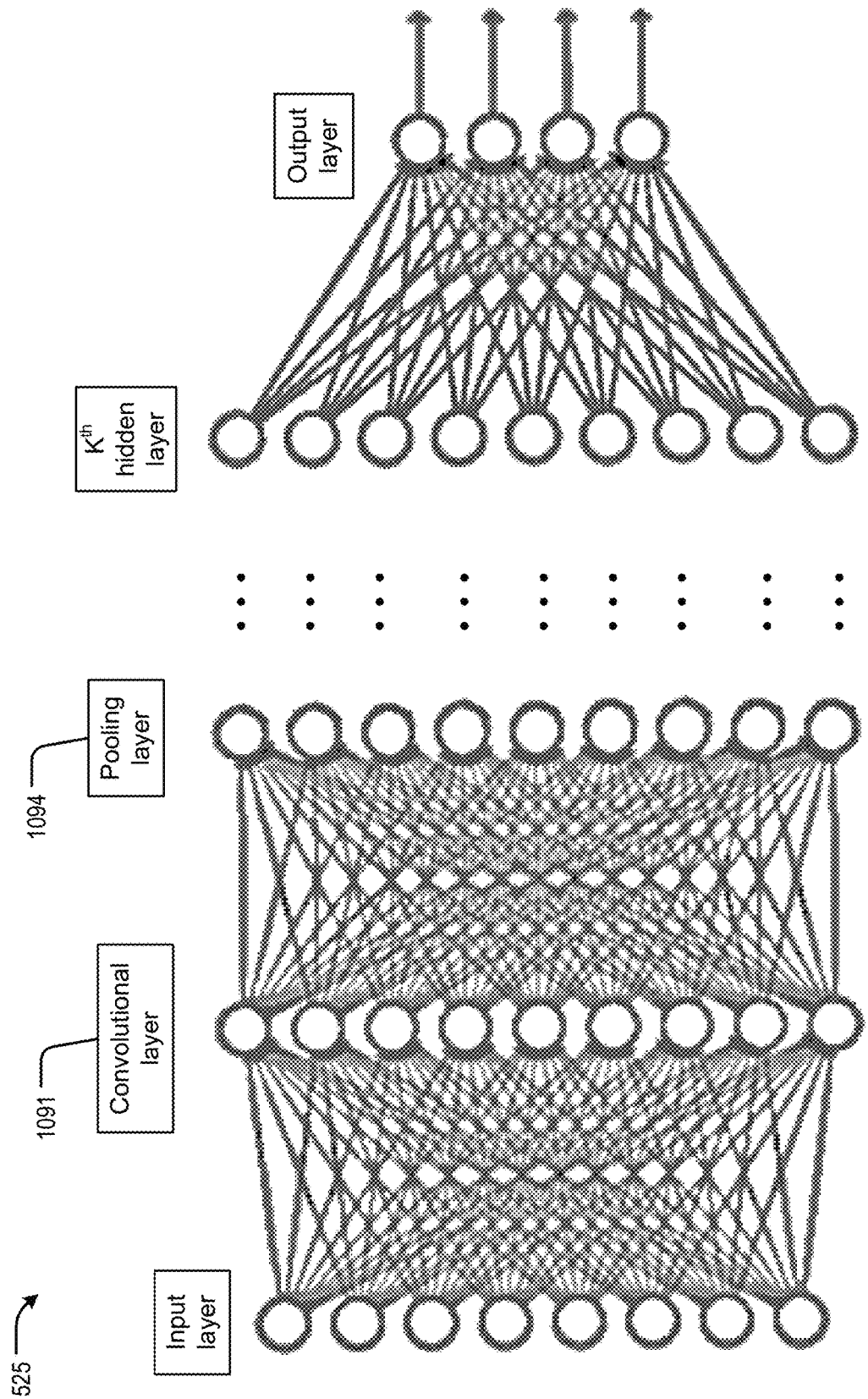
FIG. 10B is an example of a convolutional neural network, according to an embodiment of the present disclosure.

FIG. 10A and FIG. 10B show various examples of the inter-connections between layers in the P3DNN network. The P3DNN can include, in an example, fully connected layers, convolutional layers, sub sampling layers, concatenating layers, pooling layers, batch normalization layers, and activation layers, all of which are explained above and below. In certain preferred implementations of the P3DNN, convolutional layers are placed close to the input layer, whereas fully connected layers, which perform the high-level reasoning, are placed further down the architecture towards the loss function. Pooling layers can be inserted after convolutions and provide a reduction lowering the spatial extent of the filters, and thus the amount of learnable parameters. Batch normalization layers regulate gradient distractions to outliers and accelerate the learning process. Activation functions are also incorporated into various layers to introduce nonlinearity and enable the network to learn complex predictive relationships. The activation function can be a saturating activation function (e.g., a sigmoid or hyperbolic tangent activation function) or rectified activation function (e.g., ReLU discussed above). An exemplary implementation of the layered structure of the P3DNN was described with reference to FIG. 3A and FIG. 3B.

FIG. 10A shows an example of a general ANN having N inputs, K hidden layers, and three outputs. Each layer is made up of nodes (also called neurons), and each node performs a weighted sum of the inputs and compares the result of the weighted sum to a threshold to generate an output. ANNs make up a class of functions for which the members of the class are obtained by varying thresholds, connection weights, or specifics of the architecture such as the number of nodes and/or their connectivity. The nodes in an ANN can be referred to as neurons (or as neuronal nodes), and the neurons can have inter-connections between the different layers of the ANN system. The simplest ANN has three layers and is called an autoencoder. The 3D CNN can have more than three layers of neurons and have as many output neurons $\tilde{x}_N$ as input neurons, wherein N is the number of, for example, pixels in the training image volume. The synapses (i.e., the connections between neurons) store values called "weights" (also interchangeably referred to as "coefficients" or "weighting coefficients") that manipulate the data in the calculations. The "weights" of the present disclosure are described by the cascaded weight previously detailed. The outputs of the ANN depend on three types of parameters: (i) the interconnection pattern between the different layers of neurons, (ii) the learning process for updating the weights of the interconnections, and (iii) the activation function that converts a neuron's weighted input to its output activation.

Mathematically, a neuron's network function m(x) is defined as a composition of other functions $n_i(x)$, which can be further defined as a composition of other functions. This can be conveniently represented as a network structure, with arrows depicting the dependencies between variables, as shown in FIG. 10A and FIG. 10B. For example, the ANN can use a nonlinear weighted sum, wherein m(x)=K ($\Sigma_i w_i n_i$ (x)) and where K (commonly referred to as the activation function) is some predefined function, such as the hyperbolic tangent.

In FIG. 10A (and similarly in FIG. 10A), the neurons (i.e., nodes) are depicted by circles around a threshold function. For the non-limiting example shown in FIG. 10A, the inputs are depicted as circles around a linear function and the arrows indicate directed communications between neurons. In certain implementations, the P3DNN is a feedforward network.

The P3DNN of the present disclosure operates to achieve a specific task, such as estimating a high-dose medical image volume, by searching within the class of functions F to learn, using a set of observations, to find m*∈F, which solves the specific task in some optimal sense (e.g., stopping criteria). For example, in certain implementations, this can be achieved by defining a cost function C: F→m such that, for the optimal solution m*, C(m*)≤C(m)∀m ∈F (i.e., no solution has a cost less than the cost of the optimal solution). The cost function C is a measure of how far away a particular solution is from an optimal solution to the problem to be solved (e.g., the error). Learning algorithms iteratively search through the solution space to find a function that has the smallest possible cost. In certain implementations, the cost is minimized over a sample of the data (i.e., the training data).

FIG. 10B shows a non-limiting example in which the P3DNN is a CNN. CNNs are a type of ANN that have beneficial properties for image processing and, therefore, have special relevancy for applications of image denoising. CNNs use feed-forward ANNs in which the connectivity pattern between neurons can represent convolutions in image processing. For example, CNNs can be used for image-processing optimization by using multiple layers of small neuron collections which process portions of the input image, called receptive fields. The outputs of these collections can then be tiled so that they overlap to obtain a better representation of the original image. This processing pattern can be repeated over multiple layers having convolution and pooling layers, as shown, and can include batch normalization and activation layers.

As generally applied above, following after a convolution layer, a CNN can include local and/or global pooling layers which combine the outputs of neuron clusters in the convolution layers. Additionally, in certain implementations, the CNN can also include various combinations of convolutional and fully connected layers, with pointwise nonlinearity applied at the end of or after each layer.

Figure 11:
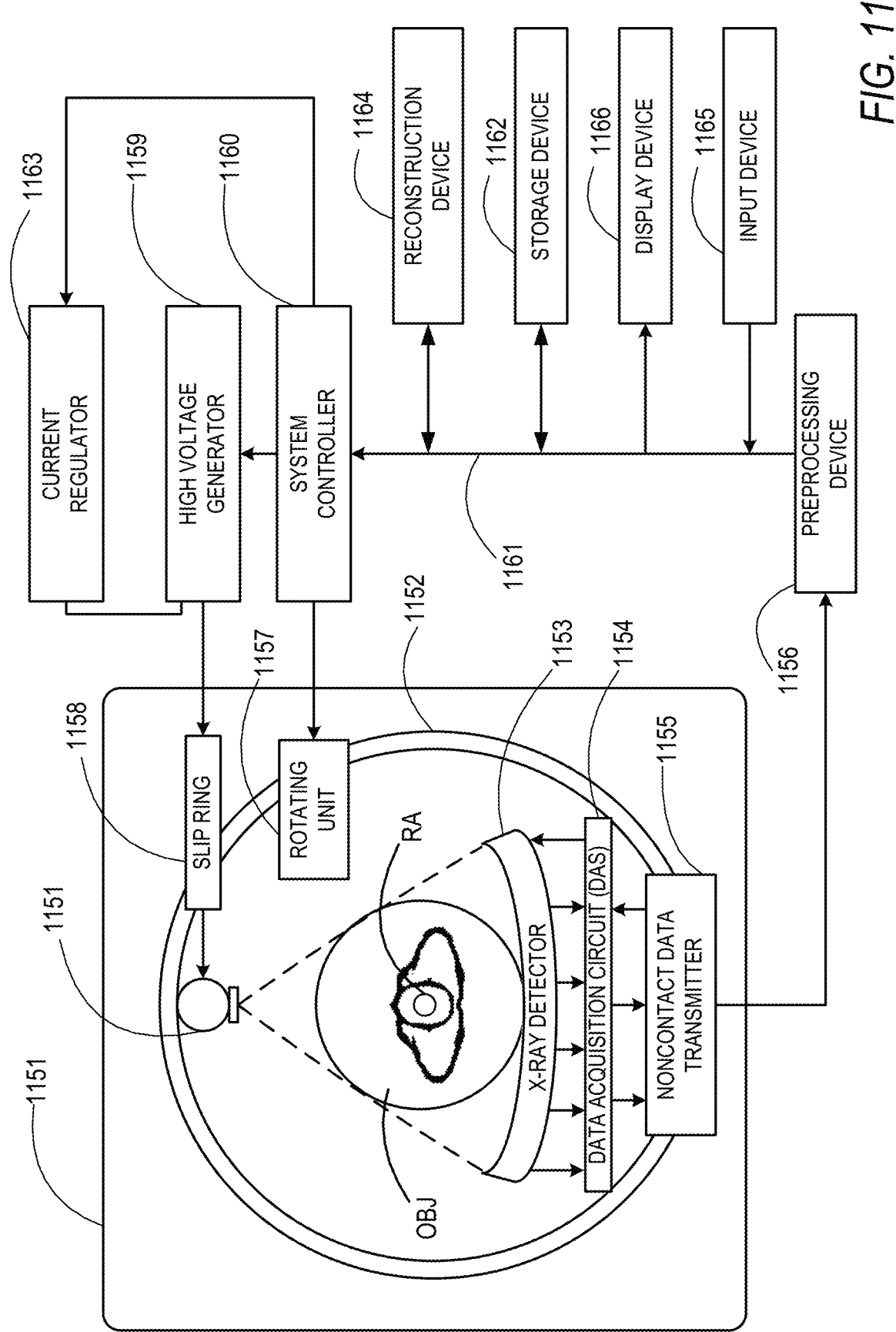
FIG. 11 is a schematic of an implementation of a computed tomography scanner in a method for improving quality of a medical image volume, according to an exemplary embodiment of the present disclosure.

According to an embodiment of the present disclosure, the above-described deep learning-based methods can be implemented as applied to data from a CT apparatus or scanner. FIG. 11 illustrates an implementation of a radiography gantry included in a CT apparatus or scanner. As shown in FIG. 11, a radiography gantry 1150 is illustrated from a side view and further includes an X-ray tube 1151, an annular frame 1152, and a multi-row or two-dimensional-array-type X-ray detector 1153. The X-ray tube 1151 and X-ray detector 1153 are diametrically mounted across an object OBJ on the annular frame 1152, which is rotatably supported around a rotation axis RA. A rotating unit 1157 rotates the annular frame 1152 at a high speed, such as 0.4 sec/rotation, while the object OBJ is being moved along the axis RA into or out of the illustrated page.

An embodiment of an X-ray CT apparatus according to the present inventions will be described below with reference to the views of the accompanying drawing. Note that X-ray CT apparatuses include various types of apparatuses, e.g., a rotate/rotate-type apparatus in which an X-ray tube and X-ray detector rotate together around an object to be examined, and a stationary/rotate-type apparatus in which many detection elements are arrayed in the form of a ring or plane, and only an X-ray tube rotates around an object to be examined. The present inventions can be applied to either type. In this case, the rotate/rotate-type, which is currently the mainstream, will be exemplified.

The multi-slice X-ray CT apparatus further includes a high voltage generator 1159 that generates a tube voltage applied to the X-ray tube 1151 through a slip ring 1158 so that the X-ray tube 1151 generates X-rays. The X-rays are emitted towards the object OBJ, whose cross-sectional area is represented by a circle. For example, the X-ray tube 1151 having an average X-ray energy during a first scan that is less than an average X-ray energy during a second scan. Thus, two or more scans can be obtained corresponding to different X-ray energies. The X-ray detector 1153 is located at an opposite side from the X-ray tube 1151 across the object OBJ for detecting the emitted X-rays that have transmitted through the object OBJ. The X-ray detector 1153 further includes individual detector elements or units.

The CT apparatus further includes other devices for processing the detected signals from the X-ray detector 1153. A data acquisition circuit or a Data Acquisition System (DAS) 1154 converts a signal output from the X-ray detector 1153 for each channel into a voltage signal, amplifies he signal, and further converts the signal into a digital signal. The X-ray detector 1153 and the DAS 1154 are configured to handle a predetermined total number of projections per rotation (TPPR).

The above-described data is sent to a preprocessing device 1156, which is housed in a console outside the radiography gantry 1150 through a non-contact data transmitter 1155. The preprocessing device 1156 performs certain corrections, such as sensitivity correction, on the raw data. A memory 1162 stores the resultant data, which is also called projection data at a stage immediately before reconstruction processing. The memory 1162 is connected to a system controller 1160 through a data/control bus 1161, together with a reconstruction device 1164, input device 1165, and display 1166. The system controller 1160 controls a current regulator 1163 that limits the current to a level sufficient for driving the CT system.

The detectors are rotated and/or fixed with respect to the patient among various generations of the CT scanner systems. In one implementation, the above-described CT system can be an example of a combined third-generation geometry and fourth-generation geometry system. In the third-generation system, the X-ray tube 1151 and the X-ray detector 1153 are diametrically mounted on the annular frame 1152 and are rotated around the object OBJ as the annular frame 1152 is rotated about the rotation axis RA. In the fourth-generation geometry system, the detectors are fixedly placed around the patient and an X-ray tube rotates around the patient. In an alternative embodiment, the radiography gantry 1150 has multiple detectors arranged on the annular frame 1152, which is supported by a C-arm and a stand.

The memory 1162 can store the measurement value representative of the irradiance of the X-rays at the X-ray detector unit 1153. Further, the memory 1162 can store a dedicated program for executing the CT image reconstruction, material decomposition, and high-dose medical image volume estimation and denoising methods including methods described herein.

The reconstruction device 1164 can execute the above-referenced methods, described herein. Further, reconstruction device 1164 can execute pre-reconstruction processing image processing such as volume rendering processing and image difference processing as needed.

The pre-reconstruction processing of the projection data performed by the preprocessing device 1156 can include correcting for detector calibrations, detector nonlinearities, and polar effects, for example.

Post-reconstruction processing performed by the reconstruction device 1164 can include filtering and smoothing the image, volume rendering processing, and image difference processing, as needed. The image reconstruction process can be performed using filtered back projection, iterative image reconstruction methods, or stochastic image reconstruction methods. The reconstruction device 1164 can use the memory to store, e.g., projection data, forward projection training data, training images, low-dose training images, calibration data and parameters, and computer programs.

The reconstruction device 1164 can include a CPU (processing circuitry) that can be implemented as discrete logic gates, as an Application Specific Integrated Circuit (ASIC), a Field Programmable Gate Array (FPGA) or other Complex Programmable Logic Device (CPLD). An FPGA or CPLD implementation may be coded in VDHL, Verilog, or any other hardware description language and the code may be stored in an electronic memory directly within the FPGA or CPLD, or as a separate electronic memory. Further, the memory 1162 can be non-volatile, such as ROM, EPROM, EEPROM or FLASH memory. The memory 1162 can also be volatile, such as static or dynamic RAM, and a processor, such as a microcontroller or microprocessor, can be provided to manage the electronic memory as well as the interaction between the FPGA or CPLD and the memory.

Alternatively, the CPU in the reconstruction device 1164 can execute a computer program including a set of computer-readable instructions that perform the functions described herein, the program being stored in any of the above-described non-transitory electronic memories and/or a hard disc drive, CD, DVD, FLASH drive or any other known storage media. Further, the computer-readable instructions may be provided as a utility application, background daemon, or component of an operating system, or combination thereof, executing in conjunction with a processor, such as a Xeon processor from Intel of America or an Opteron processor from AMD of America and an operating system, such as Microsoft 10, UNIX, Solaris, LINUX, Apple, MAC-OS and other operating systems known to those skilled in the art. Further, CPU can be implemented as multiple processors cooperatively working in parallel to perform the instructions.

In one implementation, the reconstructed images can be displayed on a display 1166. The display 1166 can be an LCD display, CRT display, plasma display, OLED, LED or any other display known in the art.

The memory 1162 can be a hard disk drive, CD-ROM drive, DVD drive, FLASH drive, RAM, ROM or any other electronic storage known in the art.

Embodiments of the subject matter and the functional operations described in this specification can be implemented in digital electronic circuitry, in tangibly embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions encoded on a tangible non-transitory program carrier for execution by, or to control the operation of data processing apparatus. Alternatively or in addition, the program instructions can be encoded on an artificially generated propagated signal, e.g., a machine-generated electrical, optical, or electromagnetic signal that is generated to encode information for transmission to suitable receiver apparatus for execution by a data processing apparatus. The computer storage medium can be a machine-readable storage device, a machine-readable storage substrate, a random or serial access memory device, or a combination of one or more of them.

The processes and logic flows described in this specification can be performed by one or more programmable computers executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application-specific integrated circuit).

Computers suitable for the execution of a computer program include, by way of example, general or special purpose microprocessors or both, or any other kind of central processing unit. Generally, a central processing unit will receive instructions and data from a read-only memory or a random access memory or both. The essential elements of a computer are a central processing unit for performing or executing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few. Computer-readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto optical disks; and CD-ROM and DVD-ROM disks. The processor and the memory can be Supplemented by, or incorporated in, special purpose logic circuitry.

Embodiments of the subject matter described in this specification can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the subject matter described in this specification, or any combination of one or more Such back-end, middleware, or front-end components. The components of the system can be interconnected by any form or medium of digital data communication, e.g., a communication network. Examples of communication networks include a local area network (LAN) and a wide area network (WAN), e.g., the Internet.

The computing system can include clients and servers. A client and server are generally remote from each other and typically interact through a communication network. The relationship of client and server arises by virtue of computer programs running on the respective computers and having a client-server relationship to each other. In some embodiments, a server transmits data, e.g., an HTML page, to a user device, e.g., for purposes of displaying data to and receiving user input from a user interacting with the user device, which acts as a client. Data generated at the user device, e.g., a result of the user interaction, can be received from the user device at the server.

While this specification contains many specific implementation details, these should not be construed as limitations on the scope of what may be claimed, but rather as descriptions of features that may be specific to particular embodiments.

Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In some cases, multitasking and parallel processing may be advantageous.

Obviously, numerous modifications and variations are possible in light of the above teachings. It is therefore to be understood that within the scope of the appended claims, the invention may be practiced otherwise than as specifically described herein.

Embodiments of the present disclosure may also be as set forth in the following parentheticals.

(1) An apparatus for improving image quality of a medical image volume, the apparatus comprising processing circuitry configured to receive a reconstructed input image volume from X-ray projection data corresponding to a three-dimensional region of an object to be examined, apply a pseudo-three-dimensional neural network to the reconstructed input image volume, the application of the pseudo-three-dimensional neural network including generating, for the reconstructed input image volume, a plurality of three-dimensional image datasets representing a different anatomical plane of the reconstructed input image volume, the plurality of three-dimensional image datasets including a sagittal plane dataset, a transverse plane dataset, and a coronal plane dataset, applying at least one convolutional filter to each of the sagittal plane dataset, the transverse plane dataset, and the coronal plane dataset, and concatenating results of the applied at least one convolutional filter to generate an intermediate output image volume, and generate, based on the application of the pseudo-three-dimensional neural network, an output image volume corresponding to the three-dimensional region of the object and having improved image quality.

(2) The apparatus of (1), wherein the at least one convolutional filter includes two convolutional filters and the processing circuitry is further configured to sequentially apply the two convolutional filters.

(3) The apparatus of either (1) or (2), wherein the at least one convolutional filter includes two convolution filters, a first convolutional filter of the two convolutional filters being a two dimensional filter and a second convolutional filter being a one dimensional filter.

(4) The apparatus of any one of (1) to (3), wherein the pseudo-three-dimensional neural network is based on a U-net architecture.

(5) The apparatus of any one of (1) to (4), wherein the pseudo-three-dimensional neural network is trained according to a cascade weight-based loss function, the cascade weight-based loss function being based on a motion artifact weight and a metal artifact weight.

(6) A method for improving image quality of a medical image volume, the method comprising receiving, by processing circuitry, a reconstructed input image volume from X-ray projection data corresponding to a three-dimensional region of an object to be examined, applying, by the processing circuitry, a pseudo-three-dimensional neural network to the reconstructed input image volume, the application of the pseudo-three-dimensional neural network including generating, by the processing circuitry and for the reconstructed input image volume, a plurality of three-dimensional image datasets representing a different anatomical plane of the reconstructed input image volume, the plurality of three-dimensional image datasets including a sagittal plane dataset, a transverse plane dataset, and a coronal plane dataset, applying, by the processing circuitry, at least one convolutional filter to each of the sagittal plane dataset, the transverse plane dataset, and the coronal plane dataset, and concatenating, by the processing circuitry, results of the applied at least one convolutional filter to generate an intermediate output image volume; and generating, by the processing circuitry and based on the application of the pseudo-three-dimensional neural network, an output image volume corresponding to the three-dimensional region of the object and having improved image quality.

(7) The method of (6), wherein the at least one convolutional filter includes two convolutional filters and the applying includes sequentially applying, by the processing circuitry, the two convolutional filters.

(8) The method of either (6) or (7), wherein the at least one convolutional filter includes two convolution filters, a first convolutional filter of the two convolutional filters being a two dimensional filter and a second convolutional filter being a one dimensional filter.

(9) The method of any one of (6) to (8), wherein the pseudo-three-dimensional neural network is based on a U-net architecture.

(10) The method of any one of (6) to (9), wherein the pseudo-three-dimensional neural network is trained according to a cascade weight-based loss function, the cascade weight-based loss function being based on a motion artifact weight and a metal artifact weight.

(11) A non-transitory computer-readable storage medium storing computer-readable instructions that, when executed by a computer, cause the computer to perform a method for improving image quality of a medical image volume, comprising receiving a reconstructed input image volume from X-ray projection data corresponding to a three-dimensional region of an object to be examined, applying a pseudo-three-dimensional neural network to the reconstructed input image volume, the application of the pseudo-three-dimensional neural network including generating, for the reconstructed input image volume, a plurality of three-dimensional image datasets representing a different anatomical plane of the reconstructed input image volume, the plurality of three-dimensional image datasets including a sagittal plane dataset, a transverse plane dataset, and a coronal plane dataset, applying at least one convolutional filter to each of the sagittal plane dataset, the transverse plane dataset, and the coronal plane dataset, and concatenating results of the applied at least one convolutional filter to generate an intermediate output image volume, and generating, based on the application of the pseudo-three-dimensional neural network, an output image volume corresponding to the three-dimensional region of the object and having improved image quality.

(12) The non-transitory computer-readable storage medium of (11), wherein the at least one convolutional filter includes two convolutional filters and the applying includes sequentially applying the two convolutional filters.

(13) The non-transitory computer-readable storage medium of either (11) or (12), wherein the at least one convolutional filter includes two convolution filters, a first convolutional filter of the two convolutional filters being a two dimensional filter and a second convolutional filter being a one dimensional filter.

(14) The non-transitory computer-readable storage medium of any one of (11) to (13), wherein the pseudo-three-dimensional neural network is based on a U-net architecture.

(15) The non-transitory computer-readable storage medium of any one of (11) to (14), wherein the pseudo-three-dimensional neural network is trained according to a cascade weight-based loss function, the cascade weight-based loss function being based on a motion artifact weight and a metal artifact weight.

Thus, the foregoing discussion discloses and describes merely exemplary embodiments of the present invention. As will be understood by those skilled in the art, the present invention may be embodied in other specific forms without departing from the spirit or essential characteristics thereof. Accordingly, the disclosure of the present invention is intended to be illustrative, but not limiting of the scope of the invention, as well as other claims. The disclosure, including any readily discernible variants of the teachings herein, defines, in part, the scope of the foregoing claim terminology such that no inventive subject matter is dedicated to the public.

The invention claimed is:

1. An apparatus for improving image quality of a medical image volume, the apparatus comprising:
   processing circuitry configured to
      receive a reconstructed input image volume from X-ray projection data corresponding to a three-dimensional region of an object to be examined,
      apply the reconstructed input image volume to a pseudo-three-dimensional neural network, the application to the pseudo-three-dimensional neural network including
         generating, from the reconstructed input image volume, a plurality of three-dimensional image datasets representing a different anatomical plane of the reconstructed input image volume, the plurality of three-dimensional image datasets including a sagittal plane dataset, a transverse plane dataset, and a coronal plane dataset,
         applying at least one convolutional filter to each of the sagittal plane dataset, the transverse plane dataset, and the coronal plane dataset, and
         concatenating results of the applied at least one convolutional filter to generate an intermediate output image volume, and
      generate, based on the application to the pseudo-three-dimensional neural network, an output image volume corresponding to the three-dimensional region of the object and having improved image quality.

2. The apparatus of claim 1, wherein the at least one convolutional filter includes two convolutional filters and the processing circuitry is further configured to sequentially apply the two convolutional filters.

3. The apparatus of claim 1, wherein the at least one convolutional filter includes two convolution filters, a first convolutional filter of the two convolutional filters being a two-dimensional filter and a second convolutional filter being a one-dimensional filter.

4. The apparatus of claim 1, wherein the pseudo-three-dimensional neural network is based on a U-net architecture.

5. The apparatus of claim 1, wherein the pseudo-three-dimensional neural network is trained according to a cascade weight-based loss function, the cascade weight-based loss function being based on a motion artifact weight and a metal artifact weight.

6. The apparatus of claim 1, wherein the processing circuitry is configured to, in generating the plurality of three-dimensional image datasets, split the reconstructed input image volume into the sagittal plane dataset, the transverse plane dataset, and the coronal plane dataset.

7. A method for improving image quality of a medical image volume, the method comprising:
   receiving, by processing circuitry, a reconstructed input image volume from X-ray projection data corresponding to a three-dimensional region of an object to be examined;
   applying, by the processing circuitry, the reconstructed input image volume to a pseudo-three-dimensional neural network, the application to the pseudo-three-dimensional neural network including
      generating, by the processing circuitry from the reconstructed input image volume, a plurality of three-dimensional image datasets representing a different anatomical plane of the reconstructed input image volume, the plurality of three-dimensional image datasets including a sagittal plane dataset, a transverse plane dataset, and a coronal plane dataset,
      applying, by the processing circuitry, at least one convolutional filter to each of the sagittal plane dataset, the transverse plane dataset, and the coronal plane dataset, and
      concatenating, by the processing circuitry, results of the applied at least one convolutional filter to generate an intermediate output image volume; and
   generating, by the processing circuitry and based on the application to the pseudo-three-dimensional neural network, an output image volume corresponding to the three-dimensional region of the object and having improved image quality.

8. The method of claim 6, wherein the at least one convolutional filter includes two convolutional filters and the applying includes sequentially applying, by the processing circuitry, the two convolutional filters.

9. The method of claim 6, wherein the at least one convolutional filter includes two convolution filters, a first convolutional filter of the two convolutional filters being a two-dimensional filter and a second convolutional filter being a one-dimensional filter.

10. The method of claim 6, wherein the pseudo-three-dimensional neural network is based on a U-net architecture.

11. The method of claim 6, wherein the pseudo-three-dimensional neural network is trained according to a cascade weight-based loss function, the cascade weight-based loss function being based on a motion artifact weight and a metal artifact weight.

12. A non-transitory computer-readable storage medium storing computer-readable instructions that, when executed by a computer, cause the computer to perform a method for improving image quality of a medical image volume, comprising:
   receiving a reconstructed input image volume from X-ray projection data corresponding to a three-dimensional region of an object to be examined;
   applying the reconstructed input image volume to a pseudo-three-dimensional neural network, the application to the pseudo-three-dimensional neural network including
      generating, from the reconstructed input image volume, a plurality of three-dimensional image datasets representing a different anatomical plane of the reconstructed input image volume, the plurality of three-dimensional image datasets including a sagittal plane dataset, a transverse plane dataset, and a coronal plane dataset, applying at least one convolutional filter to each of the sagittal plane dataset, the transverse plane dataset, and the coronal plane dataset, and concatenating results of the applied at least one convolutional filter to generate an intermediate output image volume; and generating, based on the application to the pseudo-three-dimensional neural network, an output image volume corresponding to the three-dimensional region of the object and having improved image quality.

13. The non-transitory computer-readable storage medium of claim 12, wherein the at least one convolutional filter includes two convolutional filters and the applying includes sequentially applying the two convolutional filters.

14. The non-transitory computer-readable storage medium of claim 12, wherein the at least one convolutional filter includes two convolution filters, a first convolutional filter of the two convolutional filters being a two-dimensional filter and a second convolutional filter being a one-dimensional filter.

15. The non-transitory computer-readable storage medium of claim 12, wherein the pseudo-three-dimensional neural network is based on a U-net architecture.

16. The non-transitory computer-readable storage medium of claim 12, wherein the pseudo-three-dimensional neural network is trained according to a cascade weight-based loss function, the cascade weight-based loss function being based on a motion artifact weight and a metal artifact weight.

* * * * *